United States Patent
Koka et al.

(10) Patent No.: US 11,318,298 B2
(45) Date of Patent: May 3, 2022

(54) SYSTEMS AND METHODS FOR INTRA-SURGICAL MONITORING OF COCHLEAR TRAUMA DURING AN ELECTRODE LEAD INSERTION PROCEDURE

(71) Applicant: ADVANCED BIONICS AG, Staefa (CH)

(72) Inventors: Kanthaiah Koka, Valencia, CA (US); Leonid M. Litvak, Los Angeles, CA (US)

(73) Assignee: Advanced Bionics AG, Staefa (CH)

(*) Notice: Subject to any disclaimer, the term of this patent is extended or adjusted under 35 U.S.C. 154(b) by 734 days.

(21) Appl. No.: 16/072,780

(22) PCT Filed: Jan. 27, 2016

(86) PCT No.: PCT/US2016/015203
§ 371 (c)(1),
(2) Date: Jul. 25, 2018

(87) PCT Pub. No.: WO2017/131675
PCT Pub. Date: Aug. 3, 2017

(65) Prior Publication Data
US 2019/0030323 A1     Jan. 31, 2019

(51) Int. Cl.
*A61N 1/05* (2006.01)
*A61N 1/36* (2006.01)
*A61B 5/00* (2006.01)

(52) U.S. Cl.
CPC .......... *A61N 1/0541* (2013.01); *A61B 5/6867* (2013.01); *A61N 1/36038* (2017.08)

(58) Field of Classification Search
None
See application file for complete search history.

(56) References Cited

U.S. PATENT DOCUMENTS 8,086,319 B2   12/2011   Van Dijk
9,072,468 B2   7/2015    Buchman et al.
(Continued)

FOREIGN PATENT DOCUMENTS

WO      02/32498         4/2002
WO      WO-2015054149 A1 * 4/2015 ............. H04R 25/30
(Continued)

OTHER PUBLICATIONS

Non-Final Office Action received in U.S. Appl. No. 15/768,492, dated Oct. 19, 2020.
(Continued)

*Primary Examiner* — Jay B Shah
(74) *Attorney, Agent, or Firm* — ALG Intellectual Property, LLC

(57) ABSTRACT

An exemplary monitoring system 1) monitors evoked responses that occur in response to acoustic stimulation during an insertion procedure in which a lead that is communicatively coupled to a cochlear implant is inserted into a cochlea of a patient, the monitoring comprising using an intracochlear electrode disposed on the lead to measure a first and a second evoked response at a first and a second insertion depth within the cochlea, the second insertion depth nearer to an apex of the cochlea than the first insertion depth, 2) determines that a change between the first evoked response measured at the first insertion depth and the second evoked response measured at the second insertion depth is greater than a predetermined threshold, and 3) determines, based on the determination that the change is greater than the predetermined threshold, that cochlear trauma has likely occurred at the second insertion depth.

14 Claims, 15 Drawing Sheets

(56) References Cited

U.S. PATENT DOCUMENTS

| | | | |
|---|---|---|---|
| 9,687,650 | B2 | 6/2017 | Litvak |
| 2005/0137639 | A1* | 6/2005 | Havel ................ A61N 1/3937 607/28 |
| 2005/0261748 | A1 | 11/2005 | Van Dijk |
| 2006/0089561 | A1 | 4/2006 | Eder et al. |
| 2006/0235332 | A1 | 10/2006 | Smoorenburg |
| 2006/0287690 | A1 | 12/2006 | Bouchataoui et al. |
| 2007/0167691 | A1 | 7/2007 | Causevic |
| 2007/0179565 | A1 | 8/2007 | Overstreet et al. |
| 2009/0259140 | A1* | 10/2009 | Buchman ................ A61B 5/38 600/559 |
| 2010/0030012 | A1 | 2/2010 | Meskens |
| 2010/0114288 | A1 | 5/2010 | Haller et al. |
| 2010/0198301 | A1 | 8/2010 | Smith |
| 2010/0280307 | A1 | 11/2010 | Lineaweaver et al. |
| 2011/0087085 | A1 | 4/2011 | Tsampazis et al. |
| 2011/0288613 | A1 | 11/2011 | Smith et al. |
| 2012/0143283 | A1 | 6/2012 | Polak |
| 2012/0143284 | A1 | 6/2012 | Capcelea |
| 2014/0107441 | A1 | 4/2014 | Grasso et al. |
| 2014/0276194 | A1* | 9/2014 | Osorio ................ A61B 5/377 600/554 |
| 2015/0018699 | A1 | 1/2015 | Zeng |
| 2015/0045844 | A1 | 2/2015 | Kulkarni |
| 2015/0051654 | A1 | 2/2015 | Litvak |
| 2015/0224312 | A1 | 8/2015 | Platz |
| 2015/0258337 | A1 | 9/2015 | Long |
| 2016/0016006 | A1 | 1/2016 | Boyle |
| 2016/0199368 | A1 | 7/2016 | Gosangari |

FOREIGN PATENT DOCUMENTS

| | | |
|---|---|---|
| WO | 2015/130318 | 9/2015 |
| WO | 2015/130319 | 9/2015 |
| WO | 2017/182931 | 10/2017 |

OTHER PUBLICATIONS

International Search Report and Written Opinion received in International Application No. PCT/US15/058879, dated Jun. 9, 2016.

International Search Report and Written Opinion received in International Application No. PCT/US16/015203, dated Jun. 14, 2016.

Chertoff, et al., "Analysis of the Cochlear Microphonic to a Low-Frequency Tone Embedded in Filtered Noise," The Journal of the Acoustical Society of America, 132(5), 3351-62.

Davis,, et al., "An Active Process in Cochlear Mechanics, (1983). An active process in cochlear mechanics." Hearing research, 9(1), 79-90.

Kohllöffel, et al., "Longitudinal Amplitude and Phase Distribution of the Cochlear Microphonic (Guinea Pig) and Spatial Filtering," Journal of Sound and Vibration, vol. 11, Issue 3, Mar. 1970, pp. 325-334.

Tasaki, et al., "The Space-Time Pattern of the Cochlear Microphonics (Guinea Pig)," as Recorded by Differential Electrodes, J Acoust. Soc. Am. Volume 24, Issue 5, pp. 502-519 (1952).

Final Office Action received in U.S. Appl. No. 15/768,492, dated Feb. 1, 2021.

First Office Action dated Sep. 16, 2021 in Chinese Patent Application No. 201680080337.5.

* cited by examiner

SYSTEMS AND METHODS FOR INTRA-SURGICAL MONITORING OF COCHLEAR TRAUMA DURING AN ELECTRODE LEAD INSERTION PROCEDURE

BACKGROUND INFORMATION

Insertion of an electrode lead into a cochlea of a cochlear implant patient is a delicate surgical procedure that can sometimes cause trauma or other harm to the cochlea of the patient. As a result, it may be desirable for surgeons and/or other professionals assisting with the surgical insertion procedure to monitor the cochlea during the insertion procedure to detect trauma to the cochlea in real-time as the insertion procedure takes place.

In one form of monitoring that is sometimes performed during insertion procedures, electrocochleographic ("ECoG") potentials occurring before or during the insertion procedure are monitored to track residual hearing of different areas of the cochlea as the electrode lead is inserted. However, because ECoG potentials are conventionally monitored by an electrode outside of the cochlea (e.g., at the promontory of the tympanic cavity, at the round window within the ear, at the oval window within the ear, etc.) it may be difficult or impossible to positively detect cochlear trauma based on ECoG potentials measured at these conventional placement sites. Moreover, because potentials measured outside of the cochlea are smaller than potentials that occur within the cochlea itself, potentials measured outside of the cochlea must be monitored for a relatively long period of time in order to provide enough averaging to achieve acceptable signal to noise ("SNR") ratios to derive useful information from the potentials. As a result, cochlear trauma detected from potentials measured from outside of the cochlea may be relayed to the surgeon performing the insertion procedure with undesirable or unacceptable delays. Finally, placement of an electrode outside the cochlea at the promontory of the tympanic cavity, the round window, or the oval window may obstruct the surgeon's view of the electrode lead during the insertion procedure, further complicating the procedure and increasing the risk of cochlea trauma.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
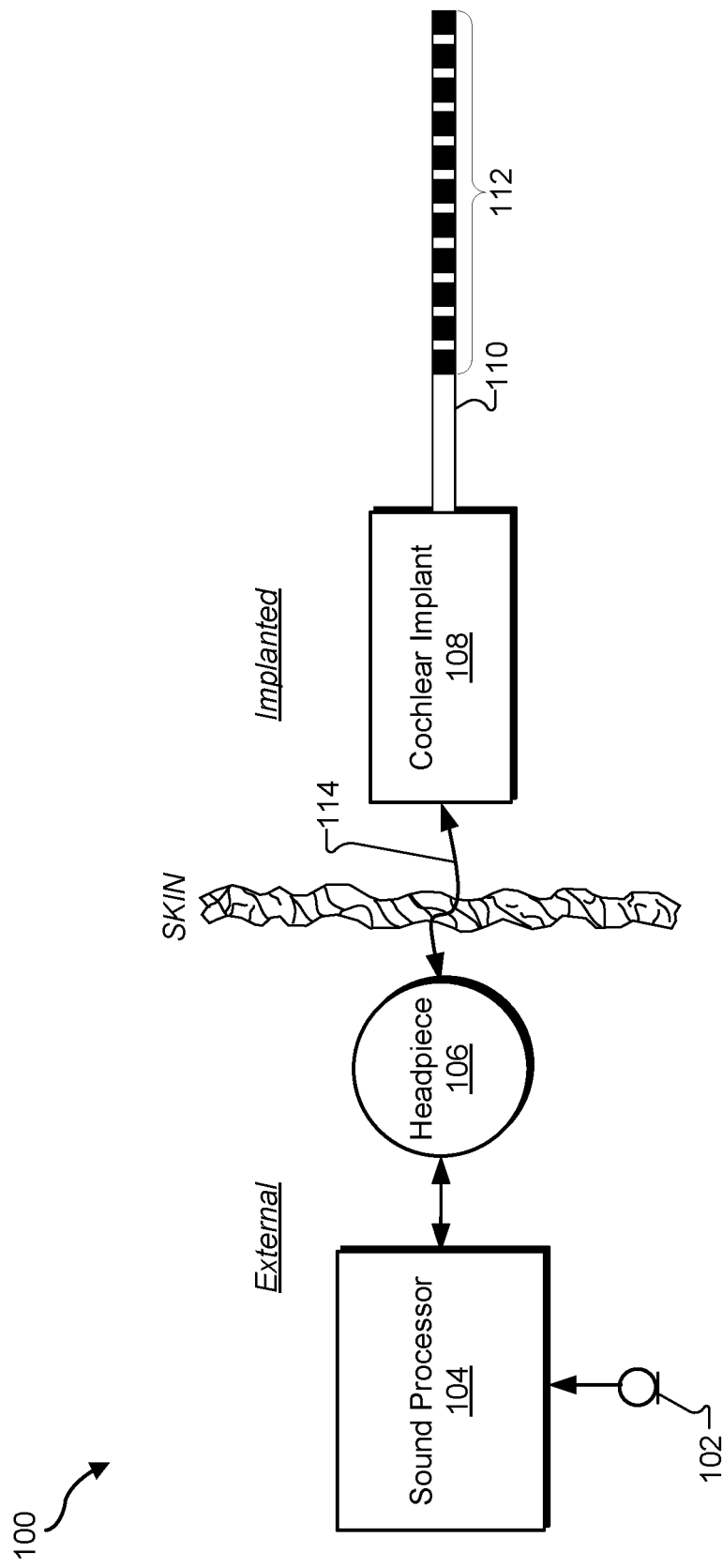
FIG. 1 illustrates an exemplary auditory prosthesis system according to principles described herein.

Systems and methods for intra-surgical monitoring of cochlear trauma during an electrode lead insertion procedure are described herein. For example, an exemplary monitoring system implemented by at least one physical computing device may monitor evoked responses that occur in response to acoustic stimulation produced at a particular frequency during an insertion procedure in which a lead that is communicatively coupled to a cochlear implant is inserted into a cochlea of a patient. As will be described below, the monitoring of the evoked responses may include using an intracochlear electrode included in a plurality of intracochlear electrodes disposed on a distal portion of the lead. The intracochlear electrode may be used to measure a first evoked response at a first insertion depth of the intracochlear electrode within the cochlea and a second evoked response at a second insertion depth of the intracochlear electrode within the cochlea, the second insertion depth nearer within the cochlea to an apex of the cochlea than the first insertion depth.

During the insertion procedure, the monitoring system may determine that a change between the first evoked response measured at the first insertion depth and the second evoked response measured at the second insertion depth is greater than a predetermined threshold. Then, during the insertion procedure and based on the determination that the change is greater than the predetermined threshold, the monitoring system may determine that cochlear trauma has likely occurred at the second insertion depth of the intracochlear electrode within the cochlea.

Because an intracochlear electrode is used in accordance with the systems and methods described herein to detect the evoked responses within the cochlea itself, cochlear trauma may be more reliably determined to have occurred at more accurate locations within the cochlea as compared to conventional systems and methods involving measuring of the evoked responses from outside the cochlea (e.g., from the promontory of the tympanic cavity, the round window, or the oval window). Moreover, the detected evoked responses may have much higher amplitudes than evoked responses detected at extracochlear locations, resulting in faster processing of the evoked responses and allowing feedback related to cochlear trauma caused by the insertion procedure to be relayed to a surgeon performing the insertion procedure in substantially real-time as the electrode lead is inserted. Additionally, the systems and methods described herein do not require an additional recording electrode not disposed on the electrode lead and that might obstruct the surgeon's view of the electrode lead during the insertion procedure.

As used herein, an "evoked response" cochlear microphonics, an auditory nerve response, a brainstem response, a compound action potential, an ECoG potential, and/or any other type of neural or physiological response that may occur within a patient in response to application of acoustic stimulation to the patient. For example, evoked responses may originate from neural tissues, hair cell to neural synapses, inner or outer hair cells, or other sources.

FIG. 1 illustrates an exemplary auditory prosthesis system 100. Auditory prosthesis system 100 may include a microphone 102, a sound processor 104, a headpiece 106 having a coil disposed therein, a cochlear implant 108, and an electrode lead 110 (also referred to as a "lead"). Lead 110 includes an array of intracochlear electrodes 112 disposed on a distal portion of lead 110 and that are configured to be located within the cochlea after lead 110 is inserted into the cochlea. While lead 110 is shown to be straight, it will be recognized that lead 110 may alternatively be pre-curved so as to fit within the cochlea. Additional or alternative components may be included within auditory prosthesis system 100 as may serve a particular implementation.

As shown, auditory prosthesis system 100 may include various components configured to be located external to a patient including, but not limited to, microphone 102, sound processor 104, and headpiece 106. Auditory prosthesis system 100 may further include various components configured to be implanted within the patient including, but not limited to, cochlear implant 108 and electrode lead 110.

Microphone 102 may be configured to detect audio signals presented to the user. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, input by way of a CPI, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may be housed within any suitable housing (e.g., a behind-the-ear ("BTE") unit, a body worn device, and/or any other sound processing unit as may serve a particular implementation).

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108 (e.g., a wireless link between a coil disposed within headpiece 106 and a coil physically coupled to cochlear implant 108). It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of cochlear implant that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites (e.g., one or more intracochlear regions) within the patient via one or more intracochlear electrodes 112 disposed along electrode lead 110. In some examples, cochlear implant 108 may include a plurality of independent current sources each associated with a channel defined by one or more of intracochlear electrodes 112. In this manner, different stimulation current levels may be applied to multiple stimulation sites simultaneously by way of multiple intracochlear electrodes 112.

Figure 2:
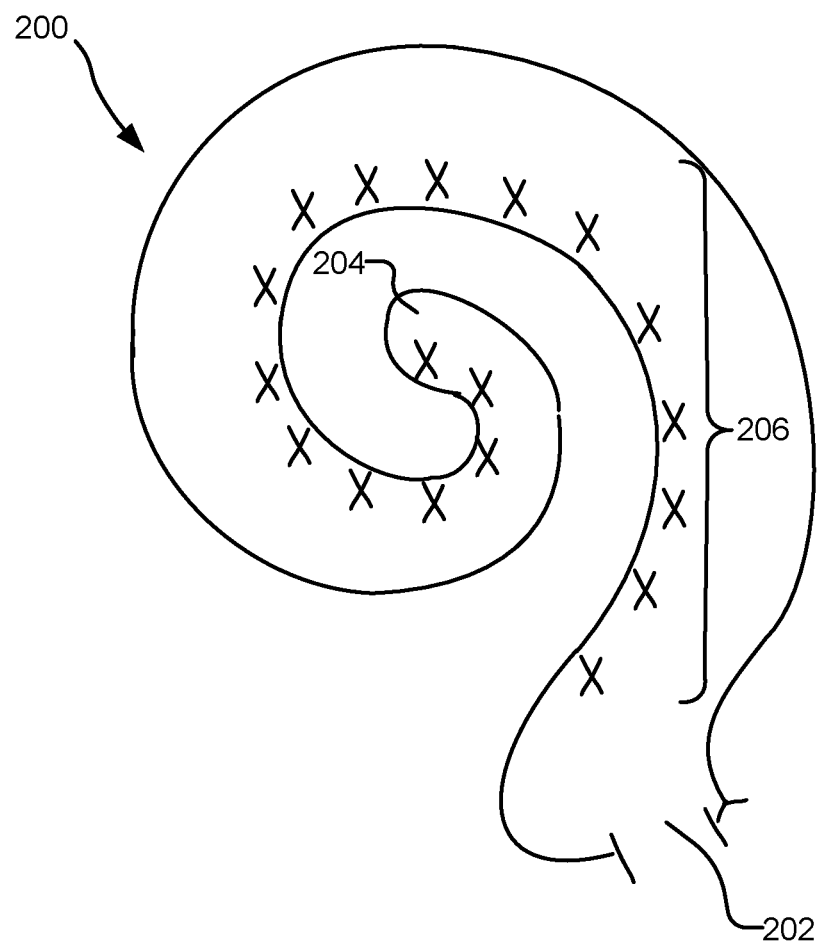
FIG. 2 illustrates a schematic structure of the human cochlea according to principles described herein.

FIG. 2 illustrates a schematic structure of the human cochlea 200 into which electrode lead 110 may be inserted. As shown in FIG. 2, cochlea 200 is in the shape of a spiral beginning at a base 202 and ending at an apex 204. Within cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, electrical stimulation applied by way of electrodes disposed within the apical region (i.e., "apical electrodes") may result in the patient perceiving relatively low frequencies and electrical stimulation applied by way of electrodes disposed within the basal region (i.e., "basal electrodes") may result in the patient perceiving relatively high frequencies. The delineation between the apical and basal electrodes on a particular electrode lead may vary depending on the insertion depth of the electrode lead, the anatomy of the patient's cochlea, and/or any other factor as may serve a particular implementation.

The auditory prosthesis system 100 illustrated in FIG. 1 may be referred to as a cochlear implant system because sound processor 104 is configured to direct cochlear implant 108 to generate and apply electrical stimulation representative of audio content (e.g., one or more audio signals) to one or more stimulation sites within the patient by way of one or more of electrodes 112.

Figure 3:
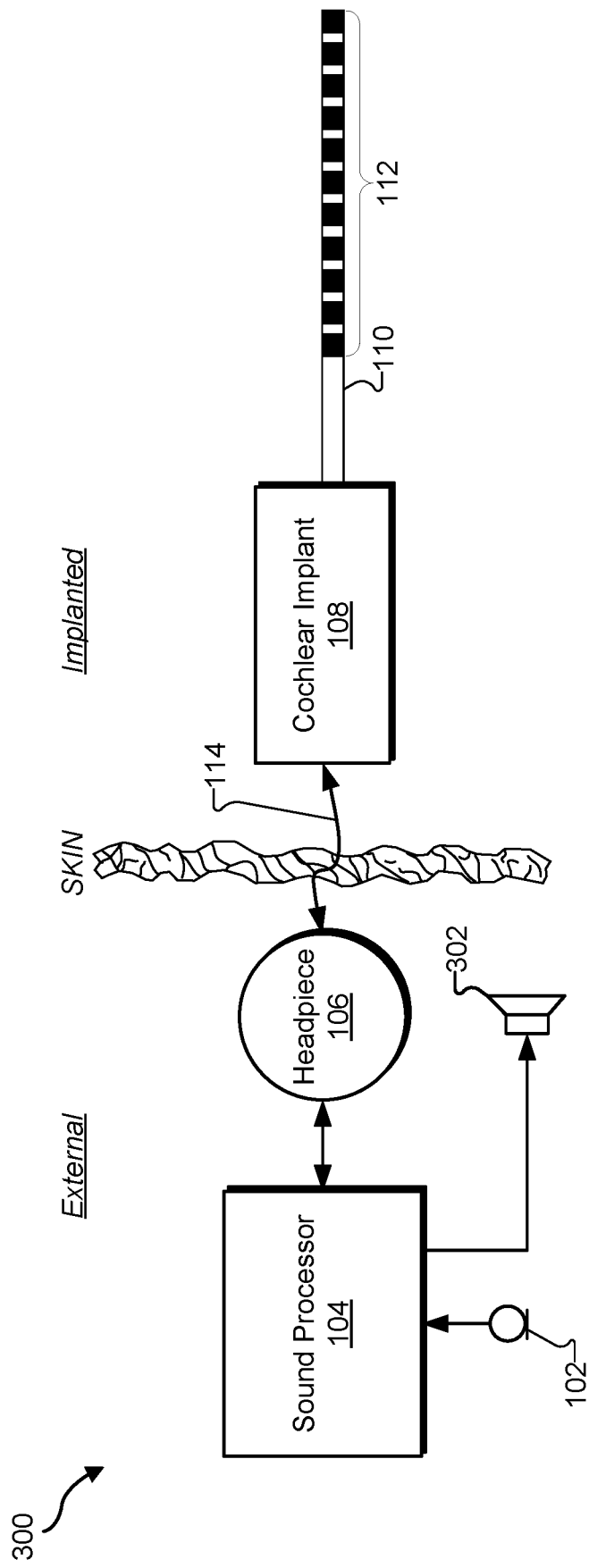
FIG. 3 illustrates an exemplary implementation of the auditory prosthesis system of FIG. 1 according to principles described herein.

FIG. 3 illustrates an exemplary implementation 300 of auditory prosthesis system 100 in which auditory prosthesis system 100 is further configured to provide acoustic stimulation to the patient. Hence, implementation 300 shown in FIG. 3 may be referred to as an electro-acoustic stimulation ("EAS") system.

As shown, implementation 300 may further include a loudspeaker 302 (also referred to as a "receiver"). Loudspeaker 302 may be in communication with an ear of the patient (e.g., located at an entrance or within the ear canal of the patient). In this configuration, sound processor 104 (which, in implementation 300, may be referred to as an "EAS sound processor") may be configured to direct loudspeaker 302 to apply acoustic stimulation representative of audio content to one or more stimulation sites within the patient (e.g., within cochlea 200, described above in relation to FIG. 2). For example, as will be described in more detail below, loudspeaker 302 may generate acoustic stimulation at a particular frequency targeted to be encoded at a particular location (e.g., at a particular target depth) within the cochlea.

In some examples, loudspeaker 302 may generate acoustic stimulation representative of audio content included in relatively low frequency bands, while cochlear implant 108 may be used to apply electrical stimulation representative of audio content included in relatively high frequency bands to one or more stimulation sites within the patient by way of one or more of intracochlear electrodes 112.

In some examples, a programming system separate from (i.e., not included within) auditory prosthesis system 100 may be selectively and communicatively coupled to sound processor 104 in order to perform one or more programming or fitting operations with respect to auditory prosthesis system 100. For example, the programming system may present audio clips to the patient by way of the auditory prosthesis system in order to facilitate evaluation of how well the auditory prosthesis system is performing for the patient.

Figure 4:
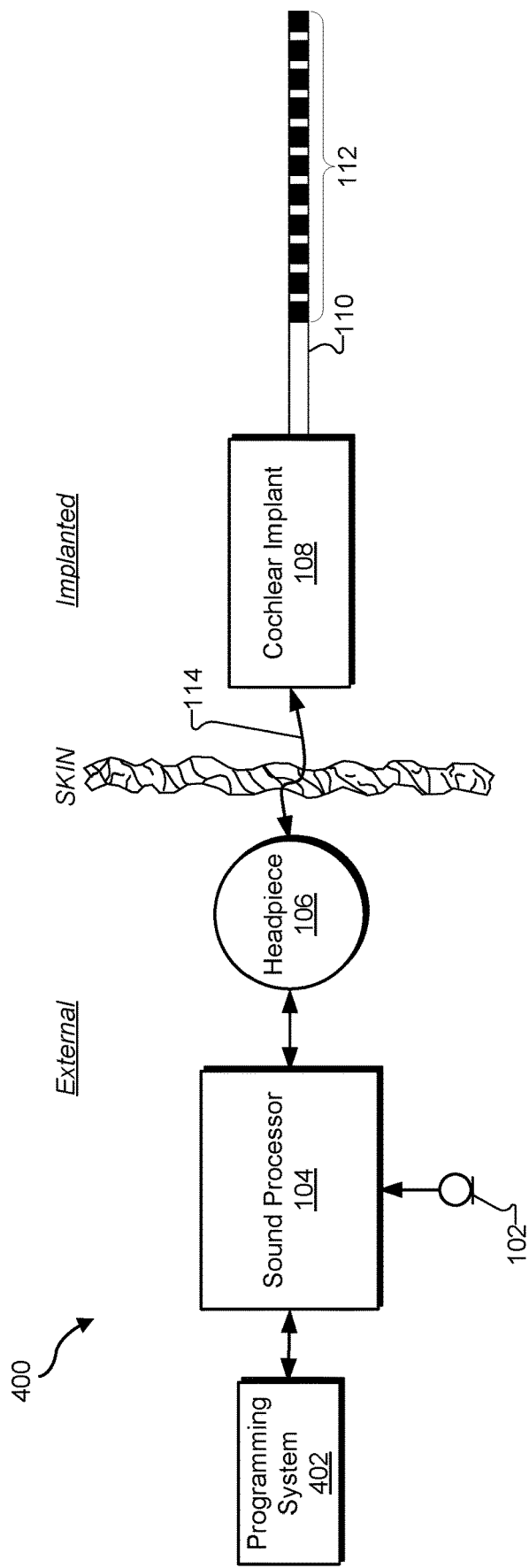
FIG. 4 illustrates an exemplary configuration in which a programming system is communicatively coupled to a sound processor according to principles described herein.

To illustrate, FIG. 4 shows an exemplary configuration 400 in which a programming system 402 is communicatively coupled (e.g., by way of a wired or wireless communication channel) to sound processor 104. Programming system 402 may be implemented by any suitable combination of physical computing and communication devices including, but not limited to, a fitting station or device, a programming device, a personal computer, a laptop computer, a handheld device, a mobile device (e.g., a mobile phone), a clinician's programming interface ("CPI") device, and/or any other suitable component as may serve a particular implementation. In some examples, programming system 402 may provide one or more graphical user interfaces ("GUIs") (e.g., by presenting the one or more GUIs by way of a display screen) with which a clinician or other user may interact.

Programming system 402 may be separate from (i.e., not included within) auditory prosthesis system 100 and may be selectively and communicatively coupled (e.g., by way of a wired or wireless communication channel) to sound processor 104 in order to perform one or more programming or fitting operations with respect to auditory prosthesis system 100. For example, programming system 402 may present audio clips to the patient by way of the auditory prosthesis system in order to facilitate evaluation of how well the auditory prosthesis system is performing for the patient.

Programming system 402 may be implemented by any suitable combination of physical computing and communication devices including, but not limited to, a fitting station or device, a programming device, a personal computer, a laptop computer, a handheld device, a mobile device (e.g., a mobile phone), a clinician's programming interface ("CPI") device, and/or any other suitable component as may serve a particular implementation. As will be described below, in some examples, programming system 402 may provide one or more graphical user interfaces ("GUIs") (e.g., by presenting the one or more GUIs by way of a display screen) with which a clinician or other user may interact.

Figure 5:
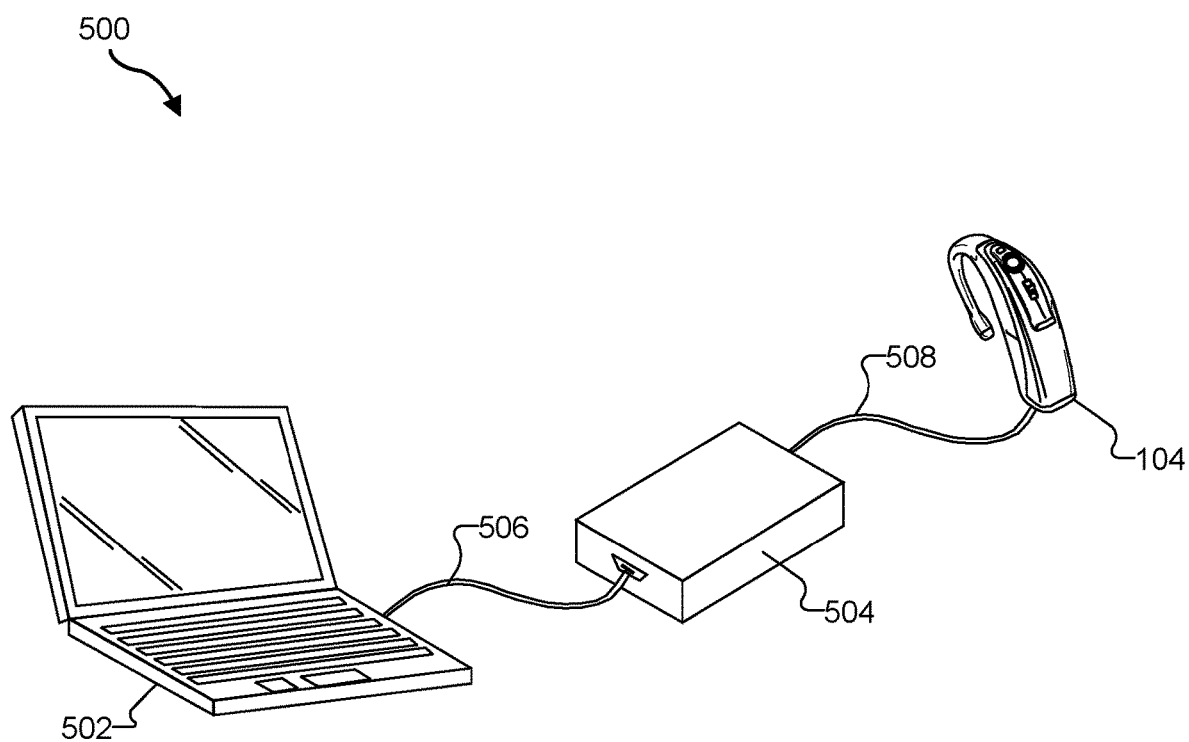
FIG. 5 illustrates an exemplary implementation of a programming system according to principles described herein.

FIG. 5 illustrates an exemplary configuration 500 in which programming system 402 is implemented by a computing device 502 and a CPI device 504. As shown, computing device 502 may be selectively and communicatively coupled to CPI device 504 by way of a cable 506. Likewise, CPI device 504 may be selectively and communicatively coupled to sound processor 104 by way of a cable 508. Cables 506 and 508 may each include any suitable type of cable that facilitates transmission of digital data between computing device 502 and sound processor 104. For example, cable 506 may include a universal serial bus ("USB") cable and cable 508 may include any type of cable configured to connect to a programming port included in sound processor 104.

Figure 6:
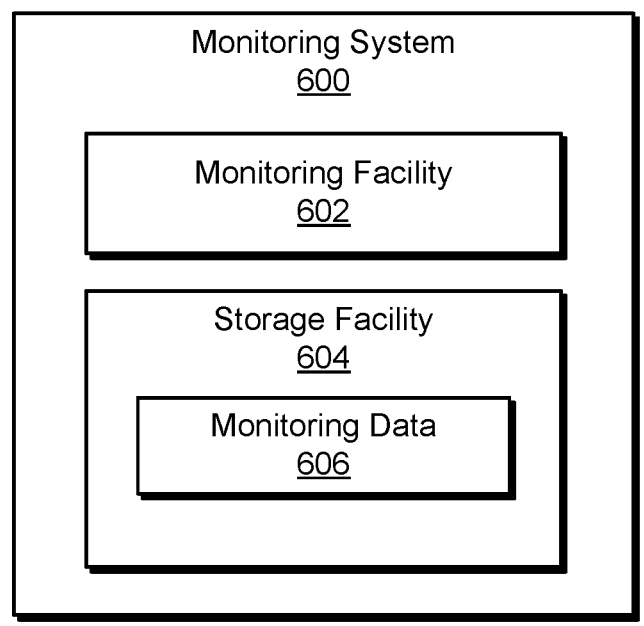
FIG. 6 illustrates exemplary components of a monitoring system according to principles described herein.

FIG. 6 illustrates exemplary components of a monitoring system 600. Monitoring system 600 may be configured to perform any of the operations described herein. As shown, monitoring system 600 may include a monitoring facility 602 and a storage facility 604, which may be in communication with one another using any suitable communication technologies. Storage facility 604 may maintain monitoring data 606 generated and/or used by monitoring facility 602. Storage facility 604 may maintain additional or alternative data as may serve a particular implementation.

Monitoring facility 602 may perform various operation associated with intra-surgical monitoring of cochlear trauma during an electrode lead insertion procedure.

For example, monitoring facility 602 may monitor evoked responses that occur in response to acoustic stimulation produced at a particular frequency during an insertion procedure in which a lead that is communicatively coupled to a cochlear implant is inserted into a cochlea of a patient. Monitoring facility 602 may monitor the evoked responses using any suitable equipment and in any way that may serve a particular implementation. For example, the monitoring of the evoked responses may be performed using an intracochlear electrode included in a plurality of intracochlear electrodes disposed on a distal portion of the lead. As will be described in more detail below, the intracochlear electrode may be shorted with an extracochlear electrode communicatively coupled with a probe that is also communicatively coupled with monitoring facility 602. As such, the intracochlear electrode may measure a first evoked response at a first insertion depth of the intracochlear electrode within the cochlea and a second evoked response at a second insertion depth of the intracochlear electrode within the cochlea (e.g., an insertion depth nearer to the apex of the cochlea) and may transmit the measurements to monitoring facility 602 via the extracochlear electrode and/or the probe.

Monitoring facility 602 may also determine, during the insertion procedure, that a change between the first evoked response measured at the first insertion depth and the second evoked response measured at the second insertion depth is greater than a predetermined threshold. For example, as will be discussed in more detail below, if the particular frequency of the acoustic stimulation is relatively low (e.g., encoded deeper within the cochlea than the lead will extend after the insertion procedure is completed), the second evoked response measured at the second insertion depth may be measured to be less than the first evoked response by an amount larger than the predetermined threshold. Additionally, if the particular frequency of the acoustic stimulation is relatively high (e.g., encoded within the cochlea at a depth that the lead will extend past after the insertion procedure is completed), the second evoked response measured at the second insertion depth may be measured to be less than the first evoked response by an amount larger than the predetermined threshold combined with an expected decrease based on the frequency (e.g., a decrease of 1/e microvolts for each millimeter beyond a target depth corresponding with the particular frequency).

During the insertion procedure (e.g., in or near real-time), monitoring facility 602 may also determine that cochlear trauma has likely occurred at the second insertion depth of the intracochlear electrode within the cochlea based on the determination that the change is greater than the predetermined threshold. In some examples, cochlear trauma may be detected based on a change in the phase of the second evoked response as compared to the phase of the first evoked response in addition to or as an alternative to a change in the amplitude of the second evoked response. Various methods of detecting cochlear trauma based on changes in amplitude or phase of evoked responses will be described in more detail below.

In various embodiments, monitoring facility 602 may perform these and various other operations that facilitate the monitoring of cochlear trauma using any component that may serve a particular implementation. For example, monitoring facility 602 may receive a user input command from a user to begin monitoring the evoked responses, present the acoustic stimulation to the patient by way of a loudspeaker (e.g., loudspeaker 302 of FIG. 3), direct a cochlear implant (e.g., cochlear implant 108 of FIG. 3) to short a particular intracochlear electrode (e.g., one of intracochlear electrodes 112) with an extracochlear electrode, receive evoked responses detected and sent by the shorted intracochlear electrode by way of the extracochlear electrode and a probe, convert signals representative of evoked responses from analog signals into digital signals, record signals representative of evoked responses (e.g., digital signals that have been converted from analog signals recorded by the intracochlear electrode), notify a user that cochlear trauma has likely occurred, and perform any other step that may serve a particular implementation.

Figure 7:
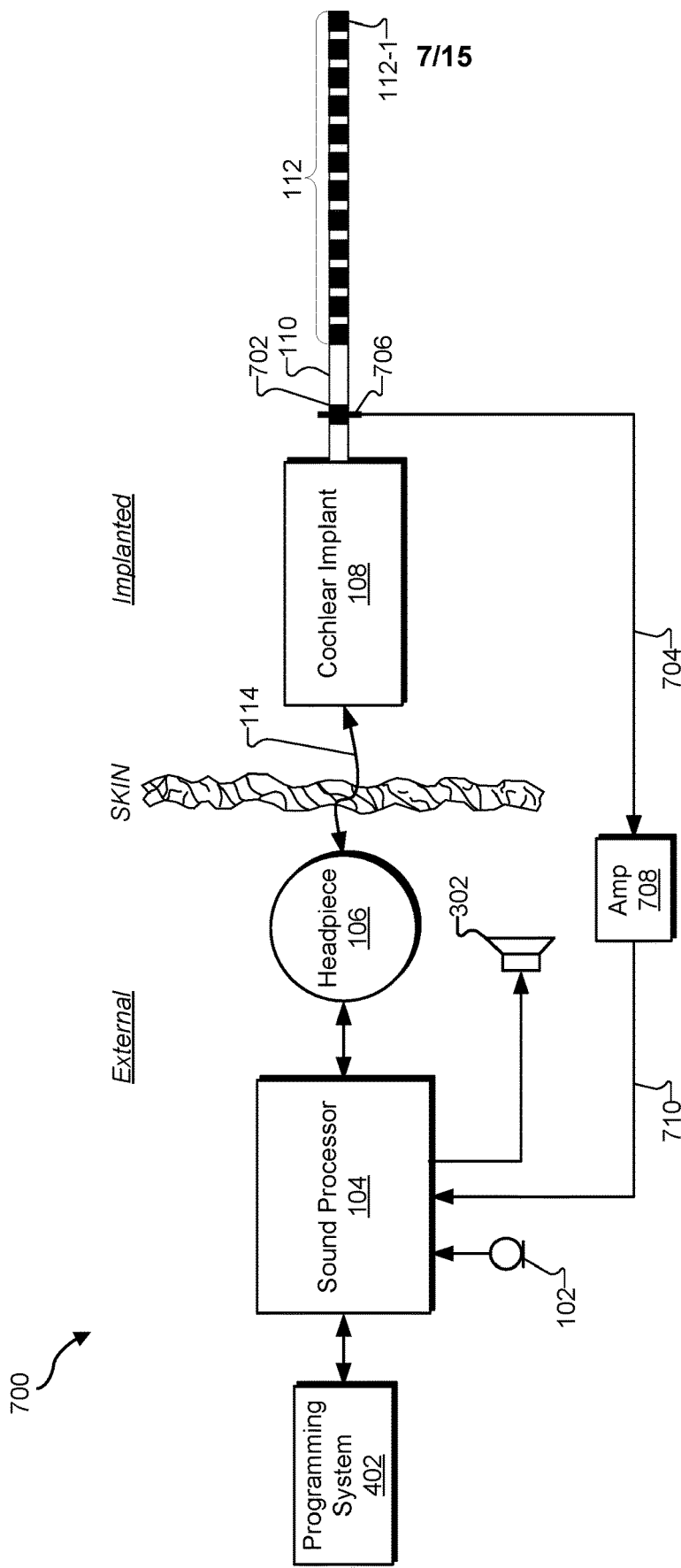
FIG. 7 illustrates an exemplary implementation of the monitoring system of FIG. 6 according to principles described herein.

To illustrate, FIG. 7 shows an exemplary implementation 700 of monitoring system 600 in which monitoring system 600 is at least partially implemented by programming system 402 and sound processor 104 included in an EAS system.

As shown in FIG. 7, sound processor 104 is physically and communicatively coupled to loudspeaker 302. As also shown in FIG. 7, an extracochlear electrode 702 may be physically and communicatively coupled to a probe 704 by way of a clip connection 706 that may be removably (i.e., temporarily) connected to extracochlear electrode 702.

Extracochlear electrode 702 may be included on lead 110 along with intracochlear electrodes 112. However, unlike intracochlear electrodes 112, extracochlear electrode 702 may be configured to be located external to the cochlea after insertion of lead 110. As such, extracochlear electrode 702 may be used, in some examples, as a return electrode for electrical stimulation applied via one or more of intracochlear electrodes 112. As will be described in more detail below, extracochlear electrode 702 may facilitate monitoring of evoked responses from within the cochlea by intracochlear electrodes 112. In some examples, extracochlear electrode 702 may comprise a ring electrode.

Probe 704 may be communicatively coupled to sound processor 104 in any suitable manner. For example, as shown in FIG. 7, a distal end of probe 704 may be physically and communicatively coupled to an amplifier 708. Amplifier 708, in turn, may be communicatively coupled to sound processor 104 by way of a communication channel 710, which may be wired or wireless. It will be recognized that amplifier 708 may, in some embodiments, be omitted from implementation 700. In these cases, probe 704 may be physically coupled directly to sound processor 104.

In some examples, a user of monitoring system 600 may provide a user input command for monitoring system 600 to begin monitoring evoked responses that occur in response to acoustic stimulation during an insertion procedure in which lead 110 is inserted into a cochlea of a patient. As described above, lead 110 may be physically and communicatively coupled to cochlear implant 108 during the insertion procedure. In response to the user input command, monitoring system 600 may begin monitoring the evoked responses as described below.

Programming system 402 may receive the user input command in any suitable manner. For example, programming system 402 may present a graphical user interface (e.g., by displaying the graphical user interface on a display screen) during the insertion procedure. The graphical user interface may include a selectable option to begin monitoring for the evoked responses. A user may select the option to provide the user input command. Specific examples of graphical user interfaces presented by programming system 402 will be described in more detail below.

Programming system 402 may transmit the user input command to sound processor 104. In response to receiving the user input command, sound processor 104 may direct cochlear implant 108 to short an intracochlear electrode included in the array of intracochlear electrodes 112 with extracochlear electrode 702. For example, sound processor 104 may direct cochlear implant 108 to short an intracochlear electrode 112-1 that is the most distal intracochlear electrode 112 of lead 110 with extracochlear electrode 702. In other examples, sound processor 104 may direct cochlear implant 108 to short any one of the other intracochlear electrodes 112 with extracochlear electrode 702 as may serve a particular implementation. Directing cochlear implant 108 to short intracochlear electrode 112-1 with extracochlear electrode 702 may be performed by transmitting a command to cochlear implant 108 by way of a wireless link that communicatively couples sound processor 104 and cochlear implant 108 (e.g., communication link 114).

In response to receiving the command from sound processor 104, cochlear implant 108 may short intracochlear electrode 112-1 with extracochlear electrode 702. Cochlear implant 108 may short intracochlear electrode 112-1 with extracochlear electrode 702 in any suitable manner. For example, cochlear implant 108 may utilize a multiplexer included within cochlear implant 108 to short intracochlear electrode 112-1 with extracochlear electrode 702. While intracochlear electrode 112-1 and extracochlear electrode 702 are shorted together, sound processor 104 may present acoustic stimulation by way of loudspeaker 302. The acoustic stimulation may include any suitable acoustic stimulation (e.g., one or more tones).

Sound processor 104 may record evoked responses that occur in response to the acoustic stimulation. For example, sound processor 104 may receive, by way of extracochlear electrode 702 and probe 704, signals representative of the evoked responses as detected and sent by intracochlear electrode 112-1. The signals detected and sent by intracochlear electrode 112-1 may be analog signals. Hence, in some examples, sound processor 104 may convert the detected analog signals to digital signals by using an analog-to-digital converter included in sound processor 104 and that is also used by sound processor 104 to convert analog audio signals detected by microphone 102 into digital audio signals.

In some examples, sound processor 104 may transmit the digital signals representative of the evoked responses to programming system 402. Programming system 402 may use the digital signals to generate and present, within a graphical user interface, graphical information associated with the evoked responses. For example, as will be described in more detail below, the graphical information may include a graph that represents amplitudes of the evoked responses, a graph that represents a current time domain waveform of the evoked responses, and/or a graph that represents a current frequency domain waveform of the evoked responses.

In some examples, the signals detected by intracochlear electrode 112-1 may be amplified by amplifier 708 prior to sound processor 104 receiving the detected signals. For example, amplifier 708 may receive the detected signals by way of extracochlear electrode 114 and probe 704. Amplifier 708 may amplify the detected signals, which may result in a plurality of amplified signals. Amplifier 708 may transmit the amplified signals to sound processor 104 by way of communication channel 710. By amplifying the signals detected by intracochlear electrode 112-1, amplifier 708 may enable sound processor 104 to more effectively and efficiently process the signals. For example, amplification by amplifier 708 may make the signals large enough to be accurately converted from the analog domain to the digital domain. It will be recognized that although amplifier 708 is shown to be a stand-alone unit located outside sound processor 104, amplifier 708 may alternatively be located within sound processor 104.

As will be described in more detail below in relation to FIGS. 8-12, while lead 110 is being inserted into the cochlea and while evoked responses are being monitored (e.g., by implementation 700 as described above), a first evoked response at a first insertion depth of intracochlear electrode 112-1 and a second evoked response at a second insertion depth of intracochlear electrode 112-1 (e.g., an insertion depth nearer within the cochlea to an apex of the cochlea than the first insertion depth) may be measured in any of the ways described herein. Based on the measurements, monitoring system 600 (e.g., including programming system 402 and/or sound processor 104) may determine that a change between the first evoked response and the second evoked response is greater than a predetermined threshold, and may further determine that that cochlear trauma has likely occurred at the second insertion depth of the intracochlear electrode within the cochlea. Based on these determinations, monitoring system 600 may notify (e.g., by an audible sound, a visible warning light, a message displayed on a graphical user interface presented by programming system 402, etc.) a user of monitoring system 600 that cochlear trauma has likely occurred at the second insertion depth of the intracochlear electrode within the cochlea.

As illustrated in FIG. 7, sound processor 104 may both present acoustic stimulation and record the evoked responses that occur in response to the acoustic stimulation. However, it will be understood that in other implementations of monitoring system 600, sound processor 104 and programming system 402 may operate in conjunction with one another in any suitable way to perform these actions and other actions described above. For example, sound processor 104 may present the acoustic stimulation while programming system 402 may record the evoked responses that occur in response to the acoustic stimulation. In another example, programming system 402 may present the acoustic stimulation while sound processor 104 may record the evoked responses that occur in response to the acoustic stimulation. In yet another example, programming system 402 may both present the acoustic stimulation and record the evoked responses that occur in response to the acoustic stimulation. In various embodiments, other devices may operate in conjunction with sound processor 104 and/or programming system 402 to perform any of the tasks described herein. For example, an evoked potential ("EP") machine (not explicitly shown in FIG. 7) may be configured to present the acoustic stimulation, to record the evoked responses that occur in response to the acoustic stimulation, or both.

Programming system 600 (e.g., embodied in implementation 700 or in another suitable implementation as described above) may monitor cochlear trauma in any suitable manner. Various examples of monitoring cochlear trauma will now be described in relation to various insertion procedures of a lead into a cochlea of a patient.

Figure 8:
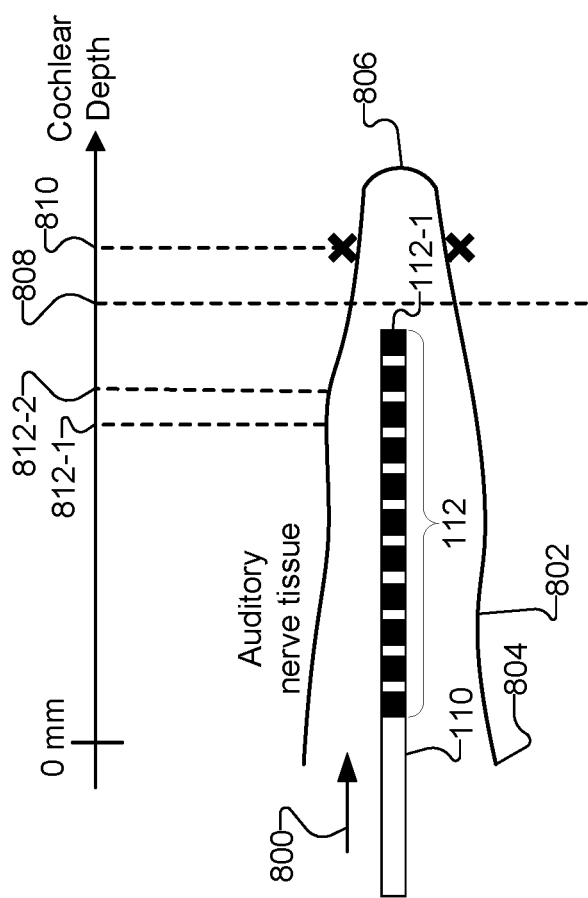
FIG. 8 illustrates an exemplary insertion procedure of an electrode lead into a cochlea of a patient according to principles described herein.

For example, FIG. 8 illustrates an exemplary insertion procedure 800 of lead 110 into a cochlea 802 of a patient. Cochlea 802 may be a cross section view of certain regions of auditory nerve tissue surrounding an inner portion of a human cochlea similar to cochlea 200, described above in relation to FIG. 2. For the sake of clarity in FIG. 8, cochlea 802 is illustrated to be uncoiled such that cochlea 802 does not exhibit the spiral shape shown for cochlea 200. However, it will be understood that cochlea 802 and lead 110 may be coiled into a spiral shape (e.g., similar to the shape shown in relation to cochlea 200) during insertion procedure 800.

It will also be understood, as mentioned above, that lead 110 may be included within a monitoring system (e.g., monitoring system 600 of FIG. 6 as implemented in implementation 700 of FIG. 7) during insertion procedure 800. For example, while omitted in FIG. 8 for clarity, lead 110 may include an extracochlear electrode (e.g., extracochlear electrode 702) that may be communicatively coupled with a probe (e.g., probe 704) by way of a clip connection (e.g., clip connection 706) that may be removably connected to the extracochlear electrode as discussed above in relation to FIG. 7. Additionally, lead 110 may be communicatively coupled with a cochlear implant (e.g., cochlear implant 108 in FIG. 7) which may receive direction from a sound processor (e.g., sound processor 104 in FIG. 7) and/or from a programming system (e.g., programming system 402 in FIG. 7), which may also be generating acoustic stimulation at a particular frequency (e.g., using loudspeaker 302 in FIG. 7) as described above. As such, one of intracochlear electrodes 112 (e.g., intracochlear electrode 112-1) may be shorted with the extracochlear electrode and may communicate evoked responses measured within cochlea 802 to the sound processor and/or to the programming system via the extracochlear electrode, the probe, and/or other components of the monitoring system (e.g., an amplifier such as amplifier 708 in FIG. 7) that may serve a particular implementation.

As shown in FIG. 8, cochlea 802 may begin at a base 804, which may be similar to base 202 of cochlea 200 in FIG. 2, and may end at an apex 806, which may be similar to apex 204 of cochlea 200. Insertion procedure 800 is represented by an arrow indicating a direction that lead 110 may be inserted into cochlea 802 during insertion procedure 800. During insertion procedure 800, lead 110 may be inserted into cochlea 802 beginning from outside base 804 until lead 110 reaches a final insertion depth 808, illustrated as a dotted line extending through cochlea 802. Accordingly, in FIG. 8, lead 110 is shown to be partially, but not fully, inserted into cochlea 802, indicating that insertion procedure 800 is ongoing.

As mentioned above, acoustic stimulation produced at a particular frequency (e.g., a tone at the particular frequency) may be generated (e.g., by a loudspeaker such as loudspeaker 302 in FIG. 7) during insertion procedure 800. Due to the tonotopic organization of auditory nerve tissue within cochlea 802 (see description in FIG. 2, above), the particular frequency may be encoded by auditory nerve tissue at a specific location (e.g., at a specific depth) within cochlea 802. For example, the auditory nerve tissue that encodes the particular frequency generated in the example of insertion procedure 800 may be encoded by auditory nerve tissue denoted by Xs in FIG. 8. Because the particular frequency in this example may be a relatively low frequency (e.g., 250 Hz), the auditory nerve tissue that encodes the particular frequency within cochlea 802 may correspond to (e.g., may be located at) a low frequency target depth 810 of cochlea 802. As shown, low frequency target depth 810 may be located nearer within cochlea 802 to apex 806 of cochlea 802 than final insertion depth 808. In other words, lead 110, including intracochlear electrode 112-1, may not pass or even reach low frequency target depth 810 during insertion procedure 800.

During insertion procedure 800, monitoring system 600 may monitor evoked responses that occur within cochlea 802 in response to the acoustic stimulation produced at the particular frequency (e.g., the relatively low frequency encoded by auditory nerve tissue located at low frequency target depth 810). More specifically, monitoring system 600 may use intracochlear electrode 112-1 to measure a first evoked response at a first insertion depth 812-1 and a second evoked response at a second insertion depth 812-2. As shown, second insertion depth 812-2 may be nearer within cochlea 802 to apex 806 (i.e. nearer according to a curved route traveled by acoustic waves through cochlea 802 rather than according to a straight route cutting directly through walls of cochlea 802) than first insertion depth 812-1.

Based on the measurements of the evoked responses at first and second insertion depths 812 and while insertion procedure 800 is still ongoing, monitoring system 600 may determine that a change between the first evoked response measured at first insertion depth 812-1 and the second evoked response measured at second insertion depth 812-2 is greater than a predetermined threshold. For example, monitoring system 600 may determine that the second evoked response is smaller in amplitude than the first evoked response by an amount greater than the predetermined threshold.

Figure 9:
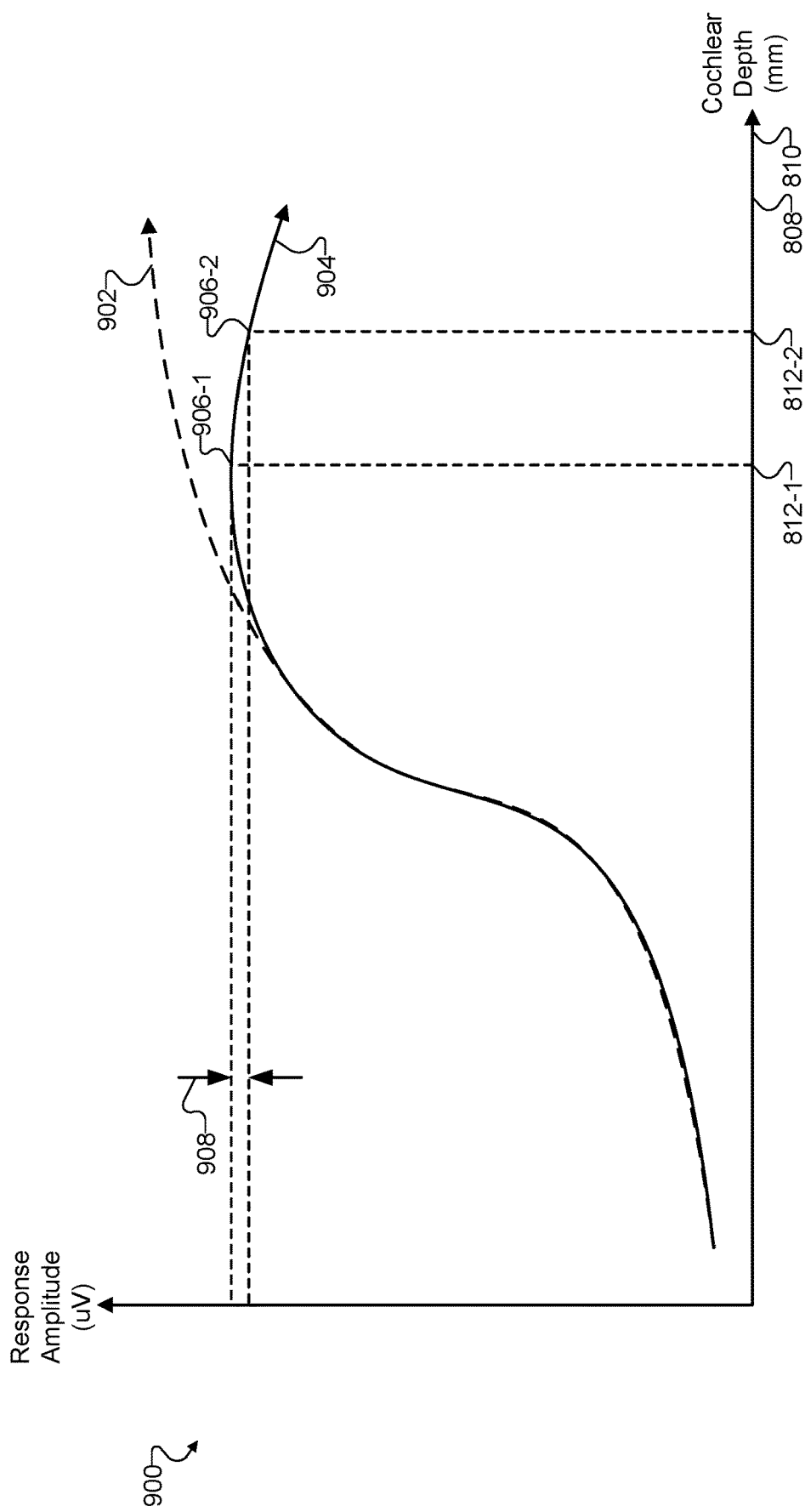
FIG. 9 illustrates an exemplary graph of evoked responses measured along the cochlea during the insertion procedure of FIG. 8 according to principles described herein.

To illustrate, FIG. 9 shows an exemplary graph 900 of evoked response curves 902 and 904 measured along cochlea 802 during insertion procedure 800. In graph 900, evoked response curves 902 and 904 are illustrated with a horizontal axis (i.e. an x-axis) representing cochlear depth within cochlea 802 (e.g., measured in millimeters ("mm")). Thus, to correspond to FIG. 8, points representing first insertion depth 812-1, second insertion depth 812-2, final insertion depth 808, and low frequency target depth 810 are shown along the horizontal axis from left to right in that order. Evoked response curves 902 and 904 are illustrated with a vertical axis (i.e. a y-axis) representing a response amplitude of the evoked response curves (e.g., measured in microvolts ("uV")). Accordingly, graph 900 illustrates how the amplitude of evoked responses (e.g., theoretical or measured evoked responses) within cochlea 802 may vary with cochlear depth (e.g., with the depth at which intracochlear electrode 112-1 is located within cochlea 802) during insertion procedure 800.

In FIG. 9, evoked response curve 902 may correspond to a theoretical (e.g., an ideal) evoked response curve representative of what monitoring system 600 would monitor in an ideal insertion procedure where no cochlear trauma is inflicted on cochlea 802. As shown, the response amplitude of evoked response curve 902 continues to increase as the cochlear depth of intracochlear electrode 112-1 increases. If monitoring system 600 monitors a continuously increasing evoked response curve such as evoked response curve 902, a surgeon performing insertion procedure 800 may know or assume that insertion procedure 800 has not caused cochlear trauma to cochlea 802 within the patient.

Conversely, evoked response curve 904 may correspond to a measured evoked response curve representative of what monitoring system 600 actually monitors during insertion procedure 800. As shown, the response amplitude of evoked response curve 904 begins to decrease at a particular cochlear depth (e.g., around first insertion depth 812-1) as the cochlear depth of intracochlear electrode 112-1 increases (e.g., as lead 110 is inserted into cochlea 802). Specifically, at first insertion depth 812-1, monitoring system 600 may monitor a first evoked response 906-1, while at second insertion depth 812-2, monitoring system 600 may monitor a second evoked response 906-2 that is smaller in amplitude than first evoked response 906-1. If a change 908 between first evoked response 906-1 and second evoked response 906-2 is greater than a predetermined threshold (e.g., 0 uV, 1 uV, 10 uV, etc.), monitoring system 600 may determine that cochlear trauma has likely occurred at a particular cochlear depth between first insertion depth 812-1 and second insertion depth 812-2. For example, monitoring system 600 may determine that cochlear trauma has likely occurred at second insertion depth 812-2. As described above in relation to FIG. 7, monitoring system 600 may, in response to detecting the likely cochlear trauma, notify a user of monitoring system 600 (e.g., the surgeon performing insertion procedure 800) that cochlear trauma has likely occurred at the particular cochlear depth between first insertion depth 812-1 and second insertion depth 812-2 (e.g., at second insertion depth 812-2) within cochlea 802.

Figure 10:
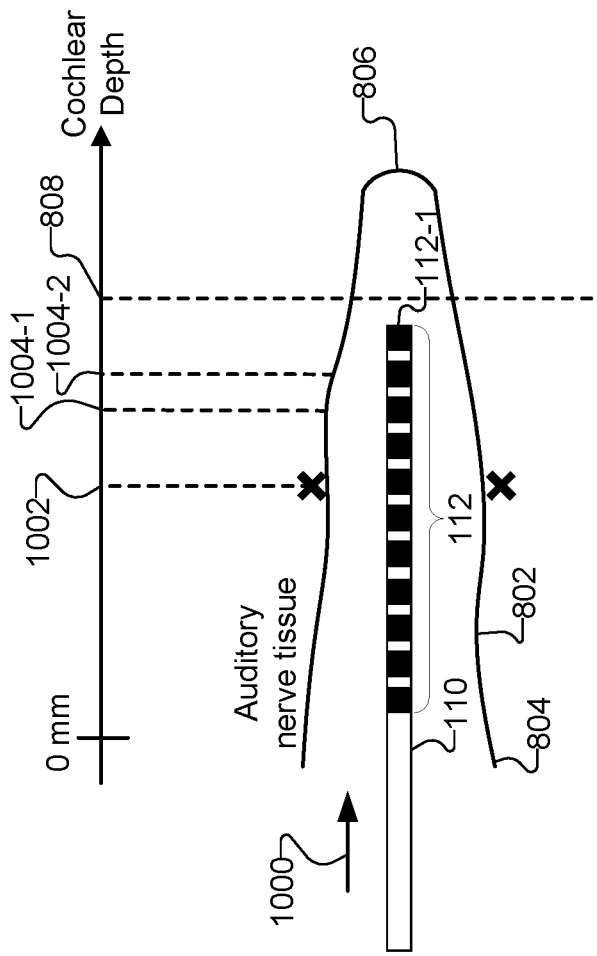
FIG. 10 illustrates an exemplary insertion procedure of an electrode lead into a cochlea of a patient according to principles described herein.

As another example of monitoring cochlear trauma, FIG. 10 illustrates an exemplary insertion procedure 1000 of lead 110 into cochlea 802 of the patient. As explained above in relation to FIG. 8, in FIG. 10, lead 110 may be included in a monitoring system (e.g., monitoring system 600 of FIG. 6 as implemented in implementation 700 of FIG. 7) during insertion procedure 1000. Again, while omitted in FIG. 10 for clarity, lead 110 may include an extracochlear electrode (e.g., extracochlear electrode 702) that may be communicatively coupled with a probe (e.g., probe 704) by way of a clip connection (e.g., clip connection 706) that may be removably connected to the extracochlear electrode as discussed above in relation to FIG. 7. Additionally, lead 110 may be communicatively coupled with a cochlear implant (e.g., cochlear implant 108 in FIG. 7) which may receive direction from a sound processor (e.g., sound processor 104 in FIG. 7) and/or from a programming system (e.g., programming system 402 in FIG. 7), which may also be generating acoustic stimulation at a particular frequency (e.g., using loudspeaker 302 in FIG. 7) as described above. As such, one of intracochlear electrodes 112 (e.g., intracochlear electrode 112-1) may be shorted with the extracochlear electrode and may communicate evoked responses measured within cochlea 802 to the sound processor and/or to the programming system via the extracochlear electrode, the probe, and/or other components of the monitoring system (e.g., an amplifier such as amplifier 708 in FIG. 7) that may serve a particular implementation.

Insertion procedure 1000 is represented by an arrow indicating a direction that lead 110 may be inserted into cochlea 802 during insertion procedure 1000. During insertion procedure 1000, lead 110 may be inserted into cochlea 802 beginning from outside base 804 until lead 110 reaches final insertion depth 808, illustrated as a dotted line extending through cochlea 802. Accordingly, in FIG. 10, lead 110 is shown to be partially, but not fully, inserted into cochlea 802, indicating that insertion procedure 1000 is ongoing.

As in previous examples, acoustic stimulation produced at a particular frequency (e.g., a tone at the particular frequency) may be generated (e.g., by a loudspeaker such as loudspeaker 302 in FIG. 7) during insertion procedure 1000. However, the particular frequency generated in the example of insertion procedure 1000 may be different (e.g., higher) than the particular frequency generated in other examples described herein. Due to the tonotopic organization of auditory nerve tissue within cochlea 802 (see description in FIG. 2, above), the particular frequency generated for insertion procedure 1000 may be encoded by auditory nerve tissue at a specific location (e.g., at a specific depth) within cochlea 802. For example, the auditory nerve tissue that encodes the particular frequency generated may be encoded by auditory nerve tissue denoted by Xs in FIG. 10. Because the particular frequency used for insertion procedure 1000 may be a relatively high frequency (e.g., 1000 Hz), the auditory nerve tissue that encodes the particular frequency within cochlea 802 may correspond to (e.g., may be located at) a high frequency target depth 1002 of cochlea 802. As shown, high frequency target depth 1002 may be located farther within cochlea 802 from apex 806 of cochlea 802 than final insertion depth 808. In other words, lead 110, including intracochlear electrode 112-1, may reach and then pass high frequency target depth 1002 during insertion procedure 1000.

During insertion procedure 1000, monitoring system 600 may monitor evoked responses that occur within cochlea 802 in response to the acoustic stimulation produced at the particular frequency (e.g., the relatively high frequency encoded by auditory nerve tissue located at high frequency target depth 1002). More specifically, monitoring system 600 may use intracochlear electrode 112-1 to measure a first evoked response at a first insertion depth 1004-1 and a second evoked response at a second insertion depth 1004-2. As shown, second insertion depth 1004-2 may be nearer within cochlea 802 to apex 806 (i.e. nearer according to a curved route traveled by acoustic waves through cochlea 802 rather than according to a straight route cutting directly through walls of cochlea 802) than first insertion depth 1004-1.

Based on the measurements of evoked responses at first and second insertion depths 1004 and while insertion procedure 1000 is still ongoing, monitoring system 600 may determine that a change between the first evoked response measured at first insertion depth 1004-1 and the second evoked response measured at second insertion depth 1004-2 is greater than a predetermined threshold. For example, monitoring system 600 may determine that the second evoked response is smaller in amplitude than the first evoked response by an amount greater than the predetermined threshold combined with an expected decrease in the second evoked response for each unit of distance beyond high frequency target depth 1002 that second insertion depth 1004-2 is located.

Figure 11:
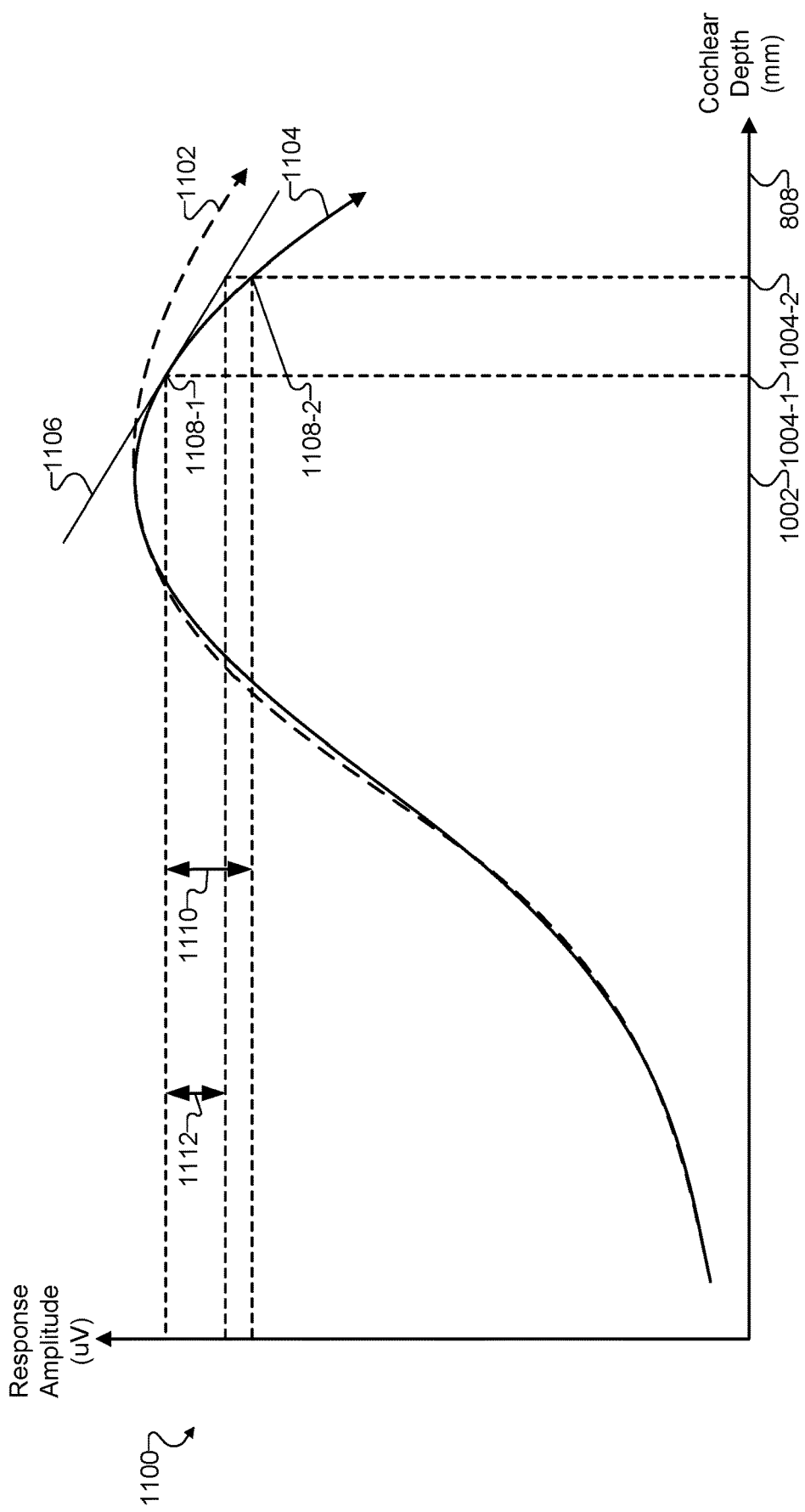
FIG. 11 illustrates an exemplary graph of evoked responses measured along the cochlea during the insertion procedure of FIG. 10 according to principles described herein.

To illustrate, FIG. 11 shows an exemplary graph 1100 of evoked response curves 1102 and 1104 measured along cochlea 802 during insertion procedure 1000. In graph 1100, evoked response curves 1102 and 1104 are illustrated with a horizontal axis (i.e. an x-axis) representing cochlear depth within cochlea 802 (e.g., measured in mm). Thus, to correspond to FIG. 10, points representing high frequency target depth 1002, first insertion depth 1004-1, second insertion depth 1004-2, and final insertion depth 808 are shown along the horizontal axis from left to right in that order. Evoked response curves 1102 and 1104 are illustrated with a vertical axis (i.e. a y-axis) representing a response amplitude of the evoked response curves (e.g., measured in uV). Accordingly, graph 1100 illustrates how the amplitude of evoked responses (e.g., theoretical or measured evoked responses) within cochlea 802 may vary with cochlear depth (e.g., with the depth at which intracochlear electrode 112-1 is located within cochlea 802) during insertion procedure 1000.

In FIG. 11, evoked response curve 1102 may correspond to a theoretical (e.g., an ideal) evoked response curve representative of what monitoring system 600 would monitor in an ideal insertion procedure where no cochlear trauma is generated on cochlea 802. As shown, the response amplitude of evoked response curve 1102 continues to increase as the cochlear depth of intracochlear electrode 112-1 increases up until high frequency target depth 1002. Then, as evoked response amplitudes are monitored at cochlear depths beyond high frequency target depth 1002, the response amplitude of evoked response curve 1102 decreases at an expected decrease rate 1106. For example, expected decrease rate 1106 may be approximately equal to $1/e$ uV/mm, where e is Euler's number (approximately equal to 2.718). Thus, expected decrease rate 1106 may be approximately equal to 0.368 uV/mm and evoked response curve 1102 may decrease approximately in parallel with expected decrease rate 1106 as shown in graph 1100. If monitoring system 600 monitors an evoked response curve that continuously increases up until high frequency target depth 1002 and decreases at expected decrease rate 1106 thereafter such as evoked response curve 1102, a surgeon performing insertion procedure 1000 may know or assume that insertion procedure 1000 has not caused cochlear trauma to cochlea 802 within the patient.

Conversely, evoked response curve 1104 may correspond to a measured evoked response curve representative of what monitoring system 600 actually monitors during insertion procedure 1000. Like evoked response curve 1102, the response amplitude of evoked response curve 1104 increases as the cochlear depth increases up until high frequency target depth 1002, whereupon the response amplitude of evoked response curve 1104 begins to decrease. However, unlike evoked response curve 1102, which decreases at approximately expected decrease rate 1106, evoked response curve 1104 begins at a particular cochlear depth (e.g., around first insertion depth 1004-1) to decrease at a rate greater than expected decrease rate 1106 as the cochlear depth of intra-cochlear electrode 112-1 increases (e.g., as lead 110 is inserted into cochlea 802). Specifically, at first insertion depth 1004-1, monitoring system 600 may monitor a first evoked response 1108-1, while at second insertion depth 1004-2, monitoring system 600 may monitor a second evoked response 1108-2 that is smaller in amplitude than first evoked response 1108-1. If a change 1110 between first evoked response 1108-1 and second evoked response 1108-2 is greater than a predetermined threshold (e.g., 0 uV, 1 uV, 10 uV, etc.) combined with an expected decrease 1112 (e.g., a decrease based on expected decrease rate 1106 for each unit of distance beyond high frequency target depth 1002 that second insertion depth 1004-2 is located), monitoring system 600 may determine that cochlear trauma has likely occurred at a particular cochlear depth between first insertion depth 1004-1 and second insertion depth 1004-2. For example, monitoring system 600 may determine that cochlear trauma has likely occurred at second insertion depth 1004-2. As described above in relation to FIG. 7, monitoring system 600 may, in response to detecting the likely cochlear trauma, notify a user of monitoring system 600 (e.g., the surgeon performing insertion procedure 1000) that cochlear trauma has likely occurred at the particular cochlear depth between first insertion depth 1004-1 and second insertion depth 1004-2 (e.g., at second insertion depth 1004-2) within cochlea 802.

As yet another example of monitoring cochlear trauma, a particular frequency may be encoded within a cochlea at a low frequency target depth of the cochlea, the low frequency target depth located nearer within the cochlea to the apex of the cochlea than a final insertion depth at which the intra-cochlear electrode is to be positioned when the insertion procedure is completed, and a monitoring system may determine that a change between a first evoked response and a second evoked response is greater than a predetermined threshold by determining that a phase of the second evoked response is different from a phase of the first evoked response by an amount greater than the predetermined threshold.

The phase of an evoked response numerically describes the relationship between timing of the evoked response (e.g., the timing of peaks of the evoked response) relative to timing of the incoming acoustic stimulation causing the evoked response (e.g., the timing of peaks of acoustic stimulation generated by loudspeaker 302). For a pure tone, the phase of the evoked response may be described in radians or degrees if the delay between input peaks (i.e. peaks of the acoustic stimulation) and output peaks (i.e. peaks of the evoked response) is scaled by the inter-peak period for each waveform. For a more complex waveform, the phase can also be described in terms of a phase delay, measured in milliseconds.

Because the phase is inherently a cyclic measure, phase delay measured based on phase alone is not unique. For example, a phase delay of P and a phase delay of P+C may result in the same phase if C represents the period of the incoming signal. Consequently, phase delay estimation may need to consider either an evoked response from an early part of the waveform (an onset response) or a more complex stimulus. The techniques for doing so shall be apparent to those skilled in the art.

In a healthy cochlea, a phase of an evoked response signal recorded within the cochlea may be expected to change methodically in accordance with the location within the cochlea (e.g., the cochlear depth) of the electrode as the electrode is inserted apically (e.g., during an insertion procedure such as insertion procedures 800 and/or 1000). Specifically, it may be expected that the phase will increase in a way that is consistent with an increasing delay as the cochlear depth of the electrode increases during the insertion procedure of the electrode into the cochlea. Additionally, as the electrode approaches and/or passes near the target frequency depth associated with the acoustic stimulation (e.g., high frequency target depth 1002), the phase may be expected to change rapidly. Specifically, at the target frequency depth, the phase may be significantly larger (e.g., 180 degrees larger) than the phase at more basal locations passed by the electrode prior to the target frequency depth during the insertion procedure. It will also be understood that the phase of the intra-cochlearly recorded signal is dependent on the health of the outer hair cells. Functioning outer hair cells sharpen the activity of the basilar membrane (especially at lower SPL levels) and increase the phase delay at almost all cochlear locations. The phase delay due to outer hair cells is particularly extenuated near the frequency target depth associated with the frequency of the acoustic stimulation.

Accordingly, a change in the phase of the intra-cochlear response during the insertion (e.g., from a first evoked response at a first cochlear depth to a second evoked response at a second cochlear depth nearer the apex of the cochlea) may be indicative of cochlear trauma. For example, a reduction in the amplitude of the response that is associated with the phase shift expected due to the location of the electrode relative to the frequency of the acoustic stimulation may be associated with normal cochlear response and not due to cochlear trauma. Conversely, a change in the phase of the evoked response without a change to amplitude of the response may be indicative of cochlear trauma. For example, if the outer hair cells are damaged, the phase of the intra-cochlear response may change in a way that is indicative of the decrease of the delay. This is because poorly functional outer hair cells may lead to decrease in the gain of the cochlear amplifier, and correspondingly a decrease in the phase delay. Because one would expect the delay to consistently increase as one progresses the recording location more apically into the cochlea, a decrease in the phase delay during the insertion may be an indicator of damage to the cochlea.

It should be noted that the changes in the phase of the response may be more specifically indicative of damage when higher frequencies and lower sound pressure levels are used for the stimulation.

To illustrate, returning to FIG. 8, a particular frequency may be encoded within cochlea 802 at low frequency target depth of cochlea 802, which is located nearer within cochlea 802 to apex 806 of cochlea 802 than final insertion depth 808. Monitoring system 600 may determine that a change between a first evoked response measured at insertion depth 812-1 and a second evoked response measured at insertion depth 812-2 is greater than a predetermined threshold. In particular, monitoring system 600 may determine that a phase of the second evoked response is different from a phase of the first evoked response by an amount greater than the predetermined threshold. If no cochlear trauma exists (e.g., if no cochlear trauma occurs during insertion procedure 800), the phase of the evoked responses measured within cochlea 802 may be expected to be constant independent of a cochlear depth at which the evoked responses are measured. As such, if monitoring system 600 detects that the phase changes from the first evoked response to the second evoked response, monitoring system 600 may determine that cochlear trauma has likely occurred at a particular location between first and second insertion depths 812 (e.g., at second insertion depth 812-2) and may notify a user (e.g., a surgeon performing insertion procedure 800) that cochlear trauma has likely occurred at a particular insertion depth between first and second insertion depths 812 (e.g., at second insertion depth 812-2).

As yet another example of monitoring cochlear trauma, monitoring system 600 may determine that a change between a first evoked response measured at a first insertion depth within the cochlea and a second evoked response measured at a second insertion depth within the cochlea, the second insertion depth nearer within the cochlea to the apex of the cochlea than the first insertion depth, is greater than a predetermined threshold. Specifically, monitoring system 600 may determine that the change is greater than the predetermined threshold by determining that the second evoked response is smaller in amplitude than the first evoked response by an amount greater than the predetermined threshold, and determining that a phase of the second evoked response is within a second predetermined threshold of a phase of the first evoked response.

Figure 12:
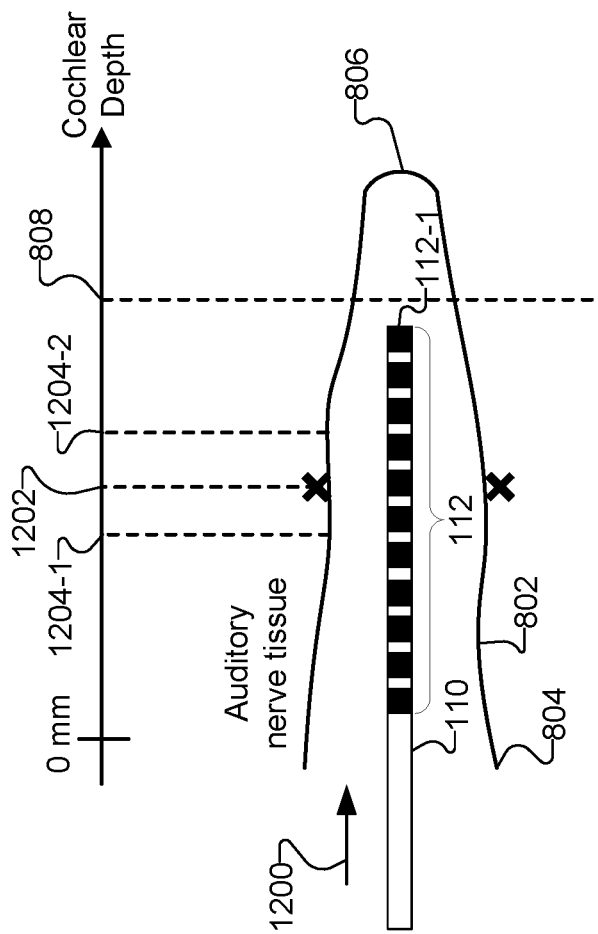
FIG. 12 illustrates an exemplary insertion procedure of an electrode lead into a cochlea of a patient according to principles described herein.

To illustrate, FIG. 12 shows an exemplary insertion procedure 1200 of lead 110 into cochlea 802 of the patient. As explained above in relation to FIGS. 8 and 10, in FIG. 12, lead 110 may be included in a monitoring system (e.g., monitoring system 600 of FIG. 6 as implemented in implementation 700 of FIG. 7) during insertion procedure 1200. Again, while omitted in FIG. 12 for clarity, lead 110 may include an extracochlear electrode (e.g., extracochlear electrode 702) that may be communicatively coupled with a probe (e.g., probe 704) by way of a clip connection (e.g., clip connection 706) that may be removably connected to the extracochlear electrode as discussed above in relation to FIG. 7. Additionally, lead 110 may be communicatively coupled with a cochlear implant (e.g., cochlear implant 108 in FIG. 7) which may receive direction from a sound processor (e.g., sound processor 104 in FIG. 7) and/or from a programming system (e.g., programming system 402 in FIG. 7), which may also be generating acoustic stimulation at a particular frequency (e.g., using loudspeaker 302 in FIG. 7) as described above. As such, one of intracochlear electrodes 112 (e.g., intracochlear electrode 112-1) may be shorted with the extracochlear electrode and may communicate evoked responses measured within cochlea 802 to the sound processor and/or to the programming system via the extracochlear electrode, the probe, and/or other components of the monitoring system (e.g., an amplifier such as amplifier 708 in FIG. 7) that may serve a particular implementation.

Insertion procedure 1200 is represented by an arrow indicating a direction that lead 110 may be inserted into cochlea 802 during insertion procedure 1200. During insertion procedure 1200, lead 110 may be inserted into cochlea 802 beginning from outside base 804 until lead 110 reaches final insertion depth 808, illustrated as a dotted line extending through cochlea 802. Accordingly, in FIG. 12, lead 110 is shown to be partially, but not fully, inserted into cochlea 802, indicating that insertion procedure 1200 is ongoing.

As in previous examples, acoustic stimulation produced at a particular frequency (e.g., a tone at the particular frequency) may be generated (e.g., by a loudspeaker such as loudspeaker 302 in FIG. 7) during insertion procedure 1200. Any suitable frequency may be used for the acoustic stimulation. For example, as shown in FIG. 12, the particular frequency used for insertion procedure may be a similar or the same relatively high frequency used in the example of insertion procedure 1000, described above. Due to the tonotopic organization of auditory nerve tissue within cochlea 802 (see description in FIG. 2, above), the particular frequency generated for insertion procedure 1200 may be encoded by auditory nerve tissue at a specific location (e.g., at a specific depth) within cochlea 802. For example, the auditory nerve tissue that encodes the particular frequency generated may be encoded by auditory nerve tissue denoted by Xs in FIG. 12. Because the particular frequency used for insertion procedure 1200 may be a relatively high frequency (e.g., 1000 Hz), the auditory nerve tissue that encodes the particular frequency within cochlea 802 may correspond to (e.g., may be located at) a high frequency target depth 1202 of cochlea 802. As shown, high frequency target depth 1202 may be located farther within cochlea 802 from apex 806 of cochlea 802 than final insertion depth 808. In other words, lead 110, including intracochlear electrode 112-1, may reach and then pass high frequency target depth 1202 during insertion procedure 1200.

During insertion procedure 1200, monitoring system 600 may monitor evoked responses that occur within cochlea 802 in response to the acoustic stimulation produced at the particular frequency (e.g., the relatively high frequency encoded by auditory nerve tissue located at high frequency target depth 1202). More specifically, monitoring system 600 may use intracochlear electrode 112-1 to measure a first evoked response at a first insertion depth 1204-1 and a second evoked response at a second insertion depth 1204-2. As shown, first insertion depth 1204-1 may be farther within cochlea 802 to apex 806 than high frequency target depth 1202, while second insertion depth 1204-2 may be nearer within cochlea 802 to apex 806 than high frequency target depth 1202.

Based on the measurements of evoked responses at first and second insertion depths 1204 and while insertion procedure 1200 is still ongoing, monitoring system 600 may determine that a change between the first evoked response measured at first insertion depth 1204-1 and the second evoked response measured at second insertion depth 1204-2 is greater than a predetermined threshold. For example, monitoring system 600 may determine that the second evoked response is smaller in amplitude than the first evoked response by an amount greater than the predetermined threshold, or greater than the predetermined threshold combined with an expected decrease in the second evoked response for each unit of distance beyond high frequency target depth 1202 that second insertion depth 1204-2 is located. Moreover, monitoring system 600 may determine that a phase of the second evoked response is within a second predetermined threshold of a phase of the first evoked response.

If no cochlear trauma exists (e.g., if no cochlear trauma occurs during insertion procedure 1200), the phase of the evoked responses measured within cochlea 802 may be expected to be constant at cochlear depths further from apex 806 than high frequency target depth 1202 and constant at cochlear depths nearer to apex 806 than high frequency target depth 1202. However, at high frequency target depth 1202, a phase at which the evoked responses are measured may change by an expected amount in an ideal insertion procedure that causes no cochlear trauma. As such, if monitoring system 600 detects that the phase does not change by at least an amount greater than the second predetermined threshold when the amplitude of the evoked response begins decreasing (e.g., when the high frequency target depth 1202 is reached), monitoring system 600 may determine that cochlear trauma has likely occurred at second insertion depth 1204-2, and may notify a user (e.g., a surgeon performing insertion procedure 1200) that cochlear trauma has likely occurred at second insertion depth 1204-2).

Figure 13:
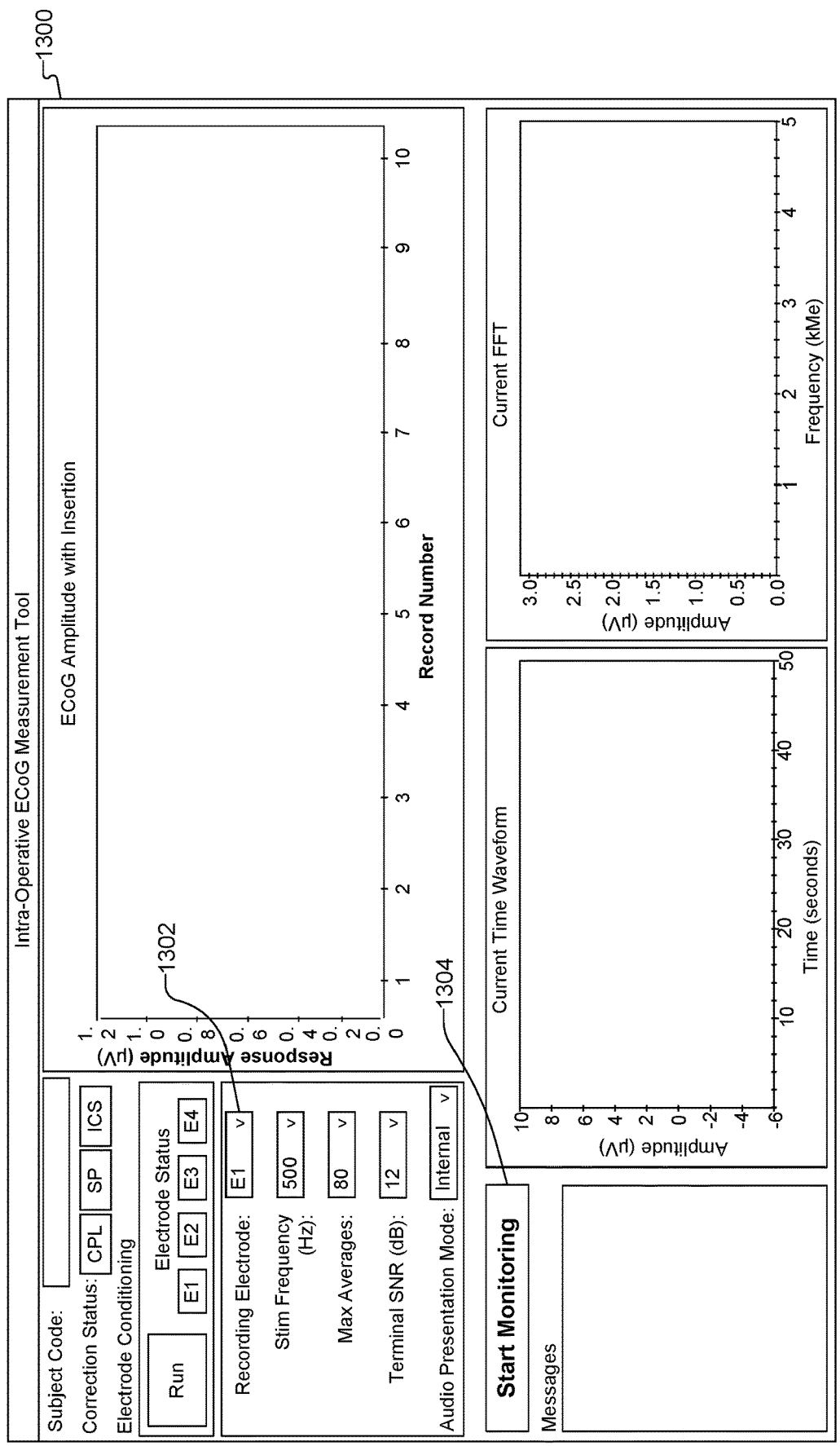
FIGS. 13-14 show exemplary graphical user interfaces according to principles described herein.

FIG. 13 shows an exemplary graphical user interface 1300 that may be presented by programming system 402 during an insertion procedure in which an electrode lead (e.g., lead 110) is inserted into a cochlea of a patient. As shown, graphical user interface 1300 includes an option 1302 (which, in this example, is a drop-down menu option) that allows a user to select which intracochlear electrode is to be shorted with the extracochlear electrode during the insertion procedure. In the particular example of FIG. 13, the user has selected an intracochlear electrode labeled "E1" to be shorted with the extracochlear electrode during the insertion procedure. For example, the intracochlear electrode labeled "E1" may correspond with intracochlear electrode 112-1 used in previous examples (e.g., see FIG. 7). The user may easily select a different intracochlear electrode for shorting by selecting, for example, the drop-down menu option 1302 and choosing a different intracochlear electrode. Graphical user interface 1300 may further include an option 1304 that may be selected by the user to provide a user input command for monitoring system 600 to begin monitoring for evoked responses.

Figure 14:
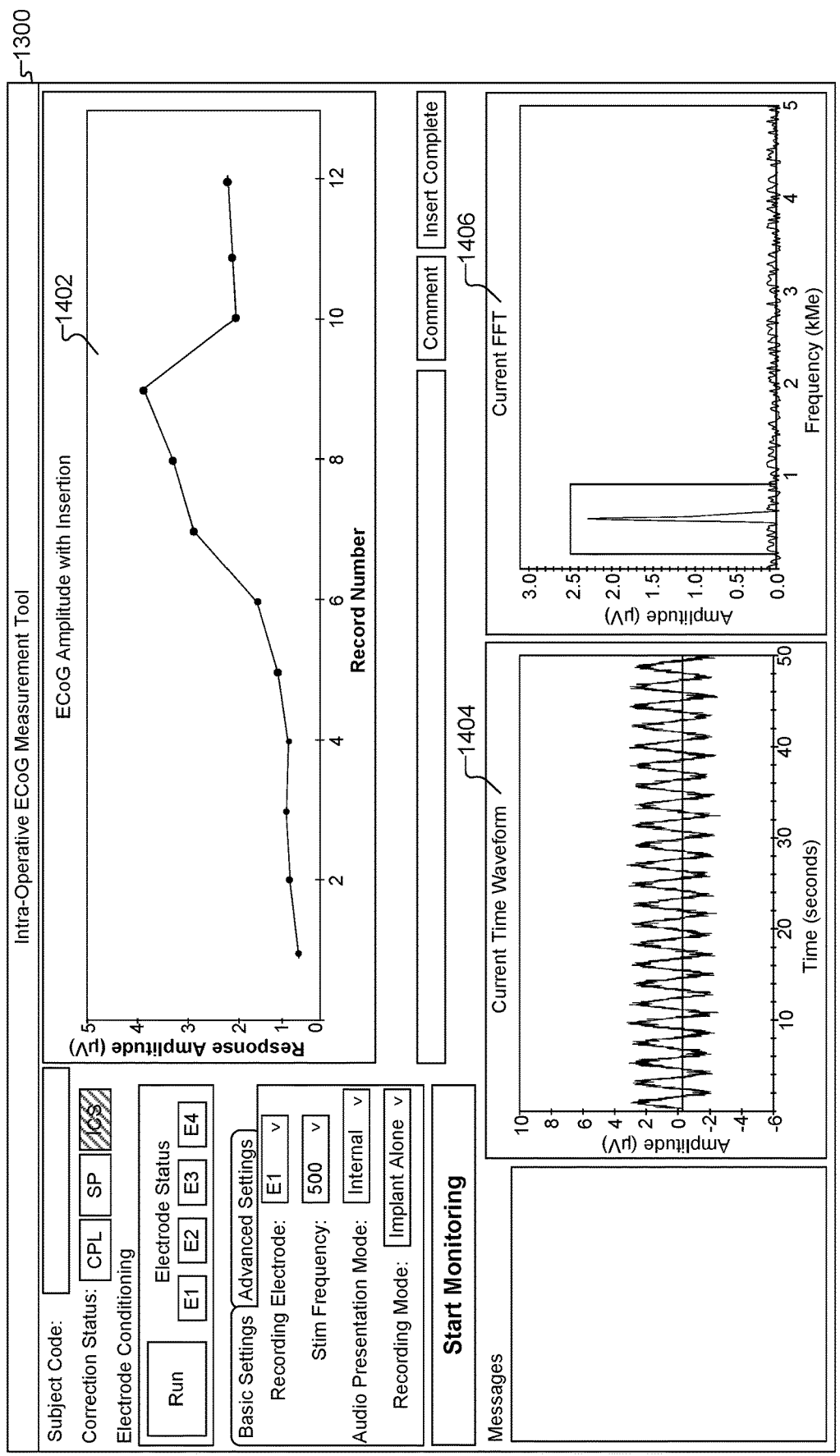

While monitoring system 600 monitors for evoked responses, programming system 402 may present, within graphical user interface 1300, graphical information associated with the evoked responses. For example, FIG. 14 shows that programming system 402 may present a graph 1402 that represents amplitudes of the evoked responses (e.g., similar to evoked response curves 902 or 904 of FIG. 9, or evoked response curves 1102 or 1104 of FIG. 11), a graph 1404 that represents a current time domain waveform of the evoked responses, and a graph 1406 that represents a current frequency domain waveform of the evoked responses. Additional or alternative graphical information associated with the evoked responses may be presented within graphical user interface 1300 as may serve a particular implementation.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a compact disc read-only memory ("CD-ROM"), a digital video disc ("DVD"), any other optical medium, random access memory ("RAM"), programmable read-only memory ("PROM"), erasable programmable read-only memory ("EPROM"), electrically erasable programmable read-only memory ("EEPROM"), a Flash EEPROM device, any other memory chip or cartridge, or any other tangible medium from which a computer can read.

Figure 15:
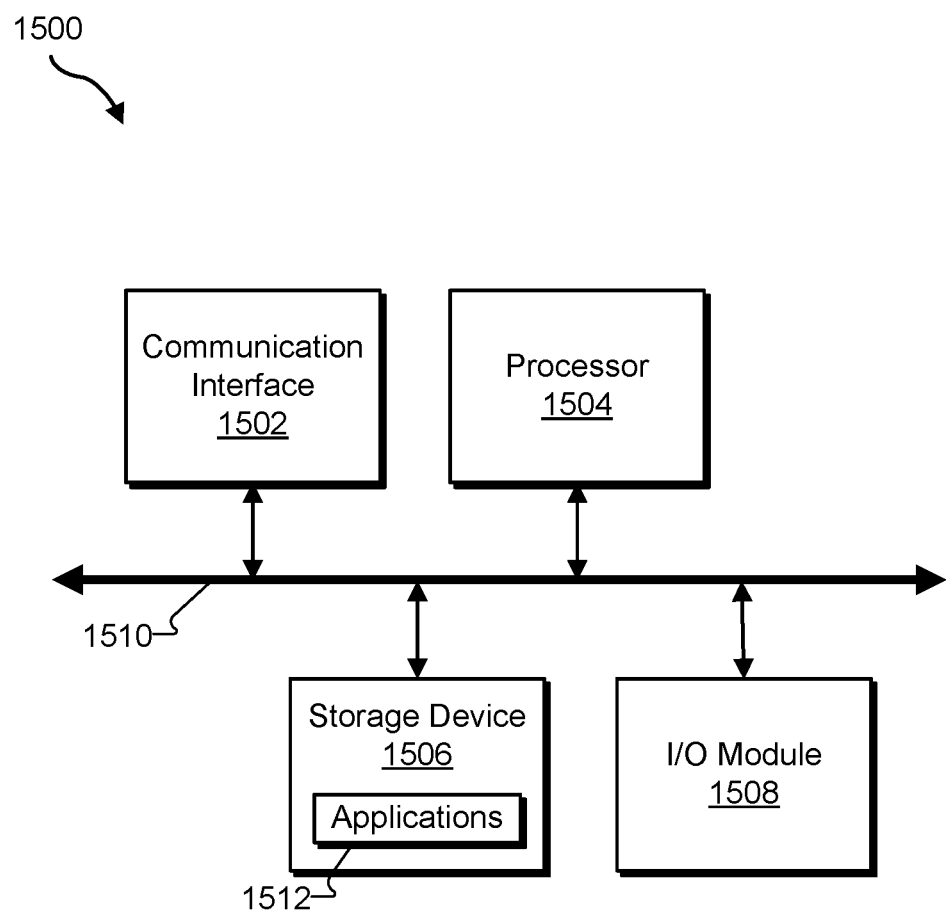
FIG. 15 illustrates an exemplary computing device according to principles described herein.

FIG. 15 illustrates an exemplary computing device 1500 that may be specifically configured to perform one or more of the processes described herein. As shown in FIG. 15, computing device 1500 may include a communication interface 1502, a processor 1504, a storage device 1506, and an input/output ("I/O") module 1508 communicatively connected via a communication infrastructure 1510. While an exemplary computing device 1500 is shown in FIG. 15, the components illustrated in FIG. 15 are not intended to be limiting. Additional or alternative components may be used in other embodiments. Components of computing device 1500 shown in FIG. 15 will now be described in additional detail.

Communication interface 1502 may be configured to communicate with one or more computing devices. Examples of communication interface 1502 include, without limitation, a wired network interface (such as a network interface card), a wireless network interface (such as a wireless network interface card), a modem, an audio/video connection, and any other suitable interface.

Processor 1504 generally represents any type or form of processing unit capable of processing data or interpreting, executing, and/or directing execution of one or more of the instructions, processes, and/or operations described herein. Processor 1504 may direct execution of operations in accordance with one or more applications 1512 or other computer-executable instructions such as may be stored in storage device 1506 or another computer-readable medium.

Storage device 1506 may include one or more data storage media, devices, or configurations and may employ any type, form, and combination of data storage media and/or device. For example, storage device 1506 may include, but is not limited to, a hard drive, network drive, flash drive, magnetic disc, optical disc, RAM, dynamic RAM, other non-volatile and/or volatile data storage units, or a combination or sub-combination thereof. Electronic data, including data described herein, may be temporarily and/or permanently stored in storage device 1506. For example, data representative of one or more executable applications 1512 configured to direct processor 1504 to perform any of the operations described herein may be stored within storage device 1506. In some examples, data may be arranged in one or more databases residing within storage device 1506.

I/O module 1508 may be configured to receive user input and provide user output and may include any hardware, firmware, software, or combination thereof supportive of input and output capabilities. For example, I/O module 1508 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1508 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1508 is configured to provide graphical data to a display for presentation to a user. The graphical data may be representative of one or more graphical user interfaces and/or any other graphical content as may serve a particular implementation.

In some examples, any of the facilities or systems described herein may be implemented by or within one or more components of computing device 1500. For example, one or more applications 1512 residing within storage device 1506 may be configured to direct processor 1504 to perform one or more processes or functions associated with monitoring facility 602. Likewise, storage facility 604 may be implemented by or within storage device 1506.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
   a cochlear implant;
   a lead configured to be coupled to the cochlear implant and to be inserted, by way of an insertion procedure, into a cochlea of a patient;
   a plurality of intracochlear electrodes disposed on a distal portion of the lead and including a particular intracochlear electrode; and
   a processor communicatively coupled with the lead by way of the cochlear implant, the processor configured to execute instructions to:
   measure, using the particular intracochlear electrode, evoked responses that occur in response to acoustic stimulation produced at a particular frequency, the evoked responses comprising:
      a first evoked response measured at a first insertion depth of the particular intracochlear electrode within the cochlea, and
      a second evoked response measured at a second insertion depth of the particular intracochlear electrode within the cochlea, the second insertion depth nearer within the cochlea to an apex of the cochlea than the first insertion depth;
   identify, during the insertion procedure, a change between the first evoked response measured at the first insertion depth and the second evoked response measured at the second insertion depth;
   determine, during the insertion procedure, that the identified change is greater than a predetermined threshold; and
   generate, during the insertion procedure and based on the determining that the identified change is greater than the predetermined threshold, a notification indicating that cochlear trauma has likely occurred at the second insertion depth of the particular intracochlear electrode within the cochlea.

2. The system of claim 1, wherein:
   the particular frequency is encoded within the cochlea at a low frequency target depth of the cochlea, the low frequency target depth located nearer within the cochlea to the apex of the cochlea than a final insertion depth at which the particular intracochlear electrode is to be positioned when the insertion procedure is completed; and
   the processor is configured to determine that the identified change between the first evoked response and the second evoked response is greater than the predetermined threshold by determining that the second evoked response is smaller in amplitude than the first evoked response by an amount greater than the predetermined threshold.

3. The system of claim 1, wherein:
   the particular frequency is encoded within the cochlea at a high frequency target depth of the cochlea, the high frequency target depth located farther within the cochlea from the apex of the cochlea than a final insertion depth at which the particular intracochlear electrode is to be positioned when the insertion procedure is completed; and
   the processor is configured to determine that the identified change between the first evoked response and the second evoked response is greater than the predetermined threshold by determining that the second evoked response is smaller in amplitude than the first evoked response by an amount greater than a sum of the predetermined threshold and an expected decrease in the second evoked response, the expected decrease determined based on a distance between the high frequency target depth and the second insertion depth.

4. The system of claim 3, wherein the expected decrease in the second evoked response is approximately 1/e microvolts for each millimeter of distance between the high frequency target depth and the second insertion depth, wherein e is Euler's number.

5. The system of claim 1, wherein:
   the particular frequency is encoded within the cochlea at a low frequency target depth of the cochlea, the low frequency target depth located nearer within the cochlea to the apex of the cochlea than a final insertion depth at which the particular intracochlear electrode is to be positioned when the insertion procedure is completed; and
   the processor is configured to determine that the identified change between the first evoked response and the second evoked response is greater than the predetermined threshold by determining that a phase of the second evoked response is different from a phase of the first evoked response by an amount greater than the predetermined threshold.

6. The system of claim 1, wherein the processor is configured to determine that the identified change between the first evoked response and the second evoked response is greater than the predetermined threshold by:
  determining that the second evoked response is smaller in amplitude than the first evoked response by an amount greater than the predetermined threshold; and
  determining that a phase of the second evoked response is within a second predetermined threshold of a phase of the first evoked response.

7. The system of claim 1, wherein the processor is further configured to execute the instructions to relay, to a surgeon performing the insertion procedure, the notification indicating that the cochlear trauma has likely occurred at the second insertion depth of the particular intracochlear electrode within the cochlea.

8. The system of claim 1, wherein the particular intracochlear electrode is configured to be located within the cochlea when the insertion procedure is completed and to detect signals representative of the evoked responses and to send the signals to the processor.

9. The system of claim 8, further comprising an extracochlear electrode disposed on the lead, the extracochlear electrode configured to be located external to the cochlea when the insertion procedure is completed;
  wherein:
    the processor is configured to measure the evoked responses by shorting the particular intracochlear electrode with the extracochlear electrode; and
    the particular intracochlear electrode sends the signals to the processor by way of the extracochlear electrode shorted with the particular intracochlear electrode and a probe physically and communicatively coupled to the extracochlear electrode and communicatively coupled to the processor.

10. The system of claim 1, wherein:
  the processor is further configured to execute the instructions to receive a user input command from a user of the system; and
  the measuring of the evoked responses is performed in response to the user input command.

11. The system of claim 1, wherein the processor is further configured to execute the instructions to:
  present the acoustic stimulation to the patient by way of a loudspeaker while the particular intracochlear electrode is within the cochlea; and
  record the evoked responses that occur in response to the acoustic stimulation by receiving signals representative of the evoked responses detected and sent by the particular intracochlear electrode.

12. The system of claim 11, wherein the processor is implemented by a sound processor included in an electro-acoustic stimulation ("EAS") system, wherein the sound processor is physically and communicatively coupled to the loudspeaker, and wherein the sound processor:
  receives a user input command from a programming system communicatively coupled to the sound processor;
  directs the cochlear implant to measure the evoked responses using the particular intracochlear electrode by transmitting a command to the cochlear implant by way of a wireless link that communicatively couples the sound processor and the cochlear implant;
  presents the acoustic stimulation by way of the loudspeaker; and
  records the evoked responses that occur in response to the acoustic stimulation by converting the signals representative of the evoked responses from analog signals into digital signals using an analog-to-digital converter included in the sound processor and that is also used by the sound processor to convert analog audio signals detected by a microphone that is communicatively coupled to the sound processor into digital audio signals.

13. The system of claim 1, further comprising a programming system configured to:
  present a graphical user interface during the insertion procedure;
  present within the graphical user interface an option for a user to select which intracochlear electrode is to be used as the particular intracochlear electrode for measuring the evoked responses during the insertion procedure;
  transmit a user input command to the processor in response to a selection by the user of an option included in the graphical user interface to begin monitoring the evoked responses; and
  display, within the graphical user interface based on digital signals representative of the evoked responses, graphical information associated with the evoked responses.

14. A method comprising:
  measuring, by a monitoring system and using a particular intracochlear electrode included in a plurality of intracochlear electrodes disposed on a distal portion of a lead coupled to a cochlear implant, evoked responses that occur in response to acoustic stimulation produced at a particular frequency during an insertion procedure in which the lead is inserted into a cochlea of a patient, the evoked responses comprising:
    a first evoked response measured at a first insertion depth of the particular intracochlear electrode within the cochlea, and
    a second evoked response measured at a second insertion depth of the particular intracochlear electrode within the cochlea, the second insertion depth nearer within the cochlea to an apex of the cochlea than the first insertion depth;
  identifying, by the monitoring system and during the insertion procedure, a change between the first evoked response measured at the first insertion depth and the second evoked response measured at the second insertion depth;
  determining, during the insertion procedure, that the identified change is greater than a predetermined threshold; and
  generating, by the monitoring system and during the insertion procedure and based on the determining that the identified change is greater than the predetermined threshold, a notification indicating that cochlear trauma has likely occurred at the second insertion depth of the particular intracochlear electrode within the cochlea.

* * * * *